(12) United States Patent
Davies et al.

(10) Patent No.: US 9,394,362 B2
(45) Date of Patent: Jul. 19, 2016

(54) IL-21 ANTIBODIES AND METHODS OF MAKING OR USING THE ANTIBODIES

(71) Applicant: Eli Lilly and Company, Indianapolis, IN (US)

(72) Inventors: Julian Davies, La Jolla, CA (US); Fabio Magrini, San Diego, CA (US); Andrea Paula Martin, Carmel, IN (US); Neelufar Mozaffarian, La Jolla, CA (US); Chetankumar N. Patel, Fishers, IN (US); Oliver Schroeder, Encinitas, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/657,075

(22) Filed: Mar. 13, 2015

(65) Prior Publication Data

US 2015/0266954 A1   Sep. 24, 2015

Related U.S. Application Data

(60) Provisional application No. 61/968,550, filed on Mar. 21, 2014.

(51) Int. Cl.
*A61K 39/395* (2006.01)
*C07K 16/24* (2006.01)
*A61K 39/00* (2006.01)

(52) U.S. Cl.
CPC ......... *C07K 16/244* (2013.01); *A61K 2039/505* (2013.01); *C07K 2317/24* (2013.01); *C07K 2317/33* (2013.01); *C07K 2317/52* (2013.01); *C07K 2317/55* (2013.01); *C07K 2317/565* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 6,258,562 B1 | 7/2001 | Salfeld et al. |
| 7,592,427 B2 | 9/2009 | Sivakumar et al. |
| 8,143,385 B2 | 3/2012 | Valge-Archer et al. |
| 8,470,979 B2 | 6/2013 | Bondensgaard et al. |
| 2009/0076249 A1 | 3/2009 | De Weers et al. |

FOREIGN PATENT DOCUMENTS

| | | |
|---|---|---|
| WO | 2010055366 | 5/2010 |
| WO | 2012098113 | 7/2012 |

OTHER PUBLICATIONS

Maurer, "Generation and Characterization of Human Anti-Human IL-21 Neutralizing Monoclonal Antibodies", mAbs, 4:1, pp. 69-83. 4:1, Jan./Feb. 2012.

*Primary Examiner* — Dong Jiang
(74) *Attorney, Agent, or Firm* — Megan N. Thobe; James J. Kelley

(57) ABSTRACT

The invention relates to engineered, humanized antibodies that have high binding affinity for and neutralize human IL-21, methods of using the antibodies to treat conditions in which antagonism or neutralization of the effects of IL-21 is warranted, such as autoimmune conditions, compositions and methods for recombinantly producing the antibodies, and pharmaceutical compositions comprising the antibodies.

27 Claims, 4 Drawing Sheets

Fig. 7A
Fig. 7B
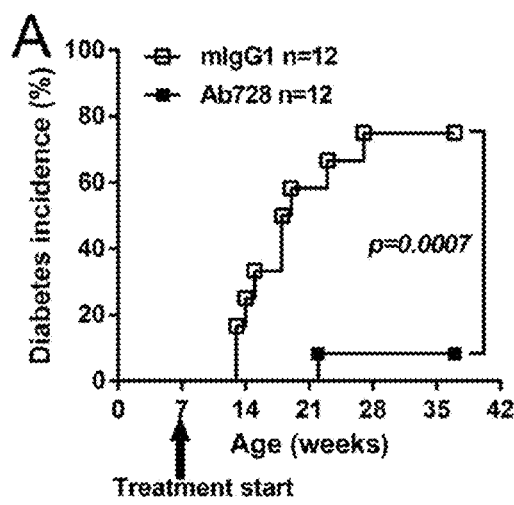
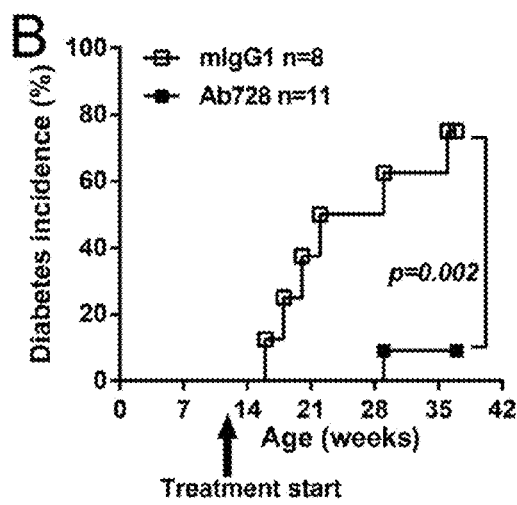

IL-21 ANTIBODIES AND METHODS OF MAKING OR USING THE ANTIBODIES

The present invention relates to engineered, humanized antibodies that have high binding affinity for and neutralize human IL-21, methods of using the antibodies to treat conditions in which antagonism or neutralization of the effects of IL-21 is warranted, such as autoimmune conditions, compositions and methods for recombinantly producing the antibodies, and pharmaceutical compositions comprising the antibodies.

WO2010/055366 discloses human antibodies derived from transgenic mice that are said to bind and neutralize human IL-21. A particular antibody is one derived from clone 362.78.

Maurer, M., et al. (Generation and characterization of human anti-human IL-21 neutralizing monoclonal antibodies, 4 MAbs 69 (2012)) describe the generation and initial characterization of a panel of human anti-human IL-21 monoclonal antibodies derived from human IgG transgenic mice, including the antibody derived from clone 362.78. Clinical studies of an anti-IL-21 antibody described in WO2010/055366, US 20130323259A1 and in Maurer et al., namely "mAb 362.78," which is also referred as NN8828 and NNC114-0006 or NNC-0000-0006, were carried out in patients having Systemic Lupus Erythematosus (SLE) and Crohn's Disease.

WO2012/098113 states that a crystal structure of human IL-21 in complex with a Fab fragment of monoclonal antibody 362.78 (NNC 0114-0005), which antibody had previously been mentioned in WO2010/055366, had been formed and analyzed using X-ray methods.

The present invention disclosed herein seeks to provide alternatives to the anti-IL-21 antibodies described above. The antibodies are potentially highly-suited to treatment of autoimmune conditions or diseases such as primary Sjögren's Syndrome (pSS), Sjögren's Syndrome (SS) and Systemic Lupus Erythematosus (SLE), Graves disease, type 1 diabetes, and others, for which few treatments are available and a medical need remains worldwide. There is a strong need for more efficacious treatments having better safety profiles than the present standards of care for patients.

In particular, the present invention provides antibodies that have as heavy and light chain variable domains the engineered and humanized heavy chain variable domain and the light chain variable domain of the antibody referred to herein as Ab327.

The present invention provides antibodies that have one or more of the following properties: 1) bind with high affinity to human IL-21 and to cynomolgous monkey IL-21 ($K_D$=0.8±0.5×10$^{-12}$ M and 0.3±0.1×10$^{-12}$ M, respectively, at 37° C. by KinExA solution equilibrium binding); 2) bind with modest affinity to mouse and rat IL-21 ($K_D$=2.4±1.3×10$^{-7}$ and 2.3±0.2×10$^{-7}$ M; respectively, at 37° C. by KinExA solution equilibrium binding); 3) do not substantially bind any other human γ-common chain family members (IL-2, IL-4, IL-7, IL-9, and IL-15); 4) neutralize human and cynomolgous monkey IL-21 activity in a particular pan-STAT-IM9-Luciferase reporter assay with an IC50 about 6-fold lower than the positive control, a hIL-21R-Fc construct (~46.7 pM and ~41 pM vs. ~271 pM, respectively); 5) neutralize human IL-21-induced proliferation of primary human B cells in vitro with an IC50 of about 1.15 nM; 6) neutralize human IL-21 induced plasma cell differentiation of primary human B cells in vitro; 7) effectively block rapid and transient expansion of several cell types in the spleen (including subpopulations of B and T cells) in mice injected with human IL-21; and/or 8) are sufficiently stable for pharmaceutical manufacturing, storage, and therapeutic use.

According to a first aspect of the present invention provides antibodies that bind to human IL-21 comprising a heavy chain variable region (HCVR) and a light chain variable region (LCVR) wherein the LCVR comprises SEQ ID NO: 7 at CDRL1, SEQ ID NO: 8 at CDRL2 and SEQ ID NO: 9 at CDRL3 and wherein the HCVR comprises SEQ ID NO: 10 at CDRH1, SEQ ID NO: 11 at CDRH2 and SEQ ID NO: 12 at CDRH3.

Preferably the antibody according to the present invention comprises an antibody heavy chain and an antibody light chain, wherein the heavy chain comprises a HCVR having the SEQ.ID.NO: 1 and wherein the light chain comprises a LCVR having the SEQ.ID.NO:2.

The present invention further provides antibodies that bind to human IL-21 comprising two antibody heavy chains and two antibody light chains, in which each heavy chain comprises a heavy chain variable domain, the amino acid sequence of which is the sequence of SEQ ID NO:1, and in which each light chain comprises a light chain variable domain, the amino acid sequence of which is the sequence of SEQ ID NO:2.

Preferably, the antibody of the present invention antibodies consists of two antibody heavy chains and two antibody light chains are provided, in which each heavy chain comprises a heavy chain variable domain, the amino acid sequence of which is the sequence of SEQ ID NO:1, and in which each light chain comprises a light chain variable domain, the amino acid sequence of which is the sequence of SEQ ID NO:2.

A particular embodiment is antibody Ab327, which is an engineered and humanized antibody to human IL-21, the amino acid sequence of each heavy chain of which is the sequence of SEQ ID NO:3 and the amino acid sequence of each light chain of which is the sequence of SEQ ID NO:4.

The present invention also provides pharmaceutical compositions comprising the antibodies of the invention and a pharmaceutically-acceptable excipient.

The present invention also includes DNA molecules encoding the heavy and light chains of the antibodies of the present invention for expressing the antibodies of the present invention. In particular, according to another aspect of the present invention there is provided a DNA molecule comprising a polynucleotide that encodes the antibody heavy chain whose amino acid sequence is the sequence of SEQ ID NO:3. The invention also provides a DNA molecule comprising a polynucleotide whose sequence is the sequence of SEQ ID NO:5. This polynucleotide sequence corresponds to the antibody heavy chain.

According to a further aspect of the present invention there is provided a DNA molecule comprising a polynucleotide that encodes the antibody light chain whose amino acid sequence is the sequence of SEQ ID NO:4. The invention further provides a DNA molecule comprising a polynucleotide whose sequence is the sequence of SEQ ID NO:6. This polynucleotide sequence corresponds to the antibody light chain.

According to a further aspect of the present invention, there is provided a DNA molecule comprising a polynucleotide that encodes the antibody heavy chain whose amino acid sequence is the sequence of SEQ ID NO:3 and comprising a polynucleotide that encodes the antibody light chain whose amino acid sequence is the sequence of SEQ ID NO:4. The present invention further provides a DNA molecule comprising a polynucleotide whose sequence is the sequence of SEQ ID NO:5 and comprising a polynucleotide whose sequence is the sequence of SEQ ID NO:6.

The present invention includes mammalian cells for expressing the antibodies of the invention by recombinant means. In particular, the present invention provides a mammalian cell transformed with a DNA molecule of the invention described above.

Another aspect of the present invention includes a process for producing an antibody, which antibody comprises two antibody heavy chains and two immunoglobulin light chains, in which the amino sequence of each of the two heavy chains is the sequence of SEQ ID NO:3 and the amino acid sequence of each of the two light chains is the sequence of SEQ ID NO:4, and which process comprises: a) cultivating a mammalian cell of the invention, as described above, under conditions such that the antibody is expressed, and b) recovering the expressed antibody. The present invention includes an antibody obtainable by the process of the invention as described immediately above.

The present invention includes methods of using the antibodies, particularly for treating autoimmune (AI) conditions, especially primary Sjögren's syndrome (pSS), Sjögren's Syndrome (SS), Systemic Lupus Erythematosus, Grave's disease, or type 1 diabetes, methods of preparing the antibodies, polynucleotides encoding the antibodies, vectors comprising the nucleotides for transforming host cells and for expressing the antibodies, host cells for expressing the antibodies, antibodies prepared by a process of recombinant expression in mammalian host systems, and pharmaceutical compositions of the antibodies that comprise the antibody and a pharmaceutically-acceptable excipient.

Particular uses envisioned for the antibodies are the treatment of AI conditions, in particular AI conditions such as primary Sjögren's syndrome (pSS), Sjögren's Syndrome (SS), systemic lupus erythematosus, Grave's disease, or type 1 diabetes. The present invention includes antibodies for use in therapy, in treating autoimmune conditions, in treating primary Sjögren's syndrome (pSS), Sjögren's Syndrome (SS), Systemic Lupus Erythematosus, Grave's disease, or type 1 diabetes, and particularly in treating primary Sjögren's syndrome (pSS), Sjögren's Syndrome (SS) or Systemic Lupus Erythematosus. The present invention includes use of an antibody of the invention for the manufacture of a medicament for use in treating an autoimmune condition; for use in treating primary Sjögren's Syndrome (pSS), Sjögren's Syndrome (SS), Systemic Lupus Erythematosus, Grave's disease, or type 1 diabetes; for treating primary Sjögren's Syndrome (pSS), Sjögren's Syndrome (SS); or for treating Systemic Lupus Erythematosus. In particular, the present invention includes the use of an antibody of the present invention in the manufacture of a medicament for the treatment of an autoimmune condition; primary Sjögren's Syndrome (pSS), Sjögren's Syndrome (pSS), Systemic Lupus Erythematosus, Grave's disease, or type 1 diabetes; primary Sjögren's Syndrome (pSS), Sjögren's Syndrome (SS); or Systemic Lupus Erythematosus.

BRIEF DESCRIPTION OF THE FIGURES

FIGS. 7A and 7B. Surrogate Antibody 728 is shown to prevent autoimmune diabetes development in NOD mice. Treatment starts at 7 weeks of age (A) as prevention or at 13 weeks of age (B) during pre-diabetic phase. Diabetic incidence is calculated per group as two consecutive readings over 250 mg/dl and displayed as percentage of diabetic mice per group (A: mIgG1 n=12; Ab728 n=12 and B: mIgG1 n=8; Ab728 n=11). Diabetes incidence is scored as survival curve data and is different by log-rank test (A: p=0.0007 and B: p=0.002).

USE OF ANTIBODIES OF THE INVENTION

Figure 1:
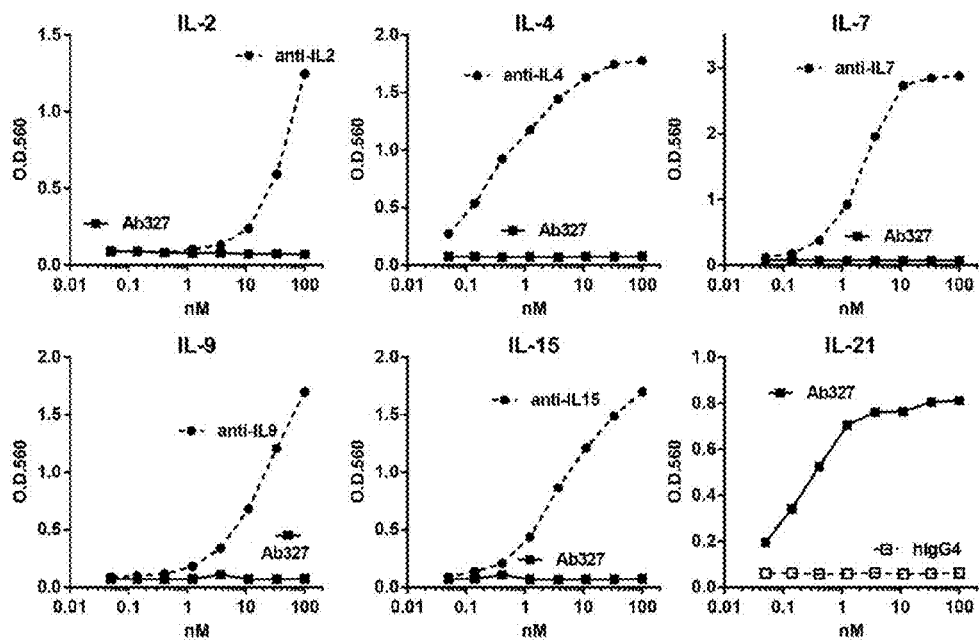
FIG. 1. Binding of Ab327 to human IL-21 and other ligands that bind human common-gamma chain receptor by ELISA is shown.

Interleukin (IL)-21 is produced by various subsets of T cells and binds to a composite receptor that consists of a specific receptor, termed IL-21 receptor (IL-21R) and the common γ-chain subunit. Human IL-21 is produced in vivo from a 162-amino acid precursor molecule. Mature human IL-21 consists of residues 30-162 (133 amino acids) of the precursor protein. Typical of class I cytokines, IL-21 has a four-helix bundle structure arranged in an up-up-down-down topology. Using the numbering of the precursor 162-amino acid protein, the helices are thought to consist of the following residues: A helix: 41-56, B helix: 69-84, C helix: 92-105, and D helix: 135-148. This structure is closely related to that of other type 1 cytokine family members, most notably IL-2, IL-4, and IL-15.

Upon binding of IL-21 to the receptor complex and subsequent receptor activation, signaling occurs through the Jak-STAT signaling pathway. The IL-21R chain binds IL-21 with high affinity and provides the majority of the binding energy. However, interaction with the common γ-chain is required for signaling. The interaction between IL-21 and IL-21R is mediated by residues present in the A and C helices and by a small part of the CD loop immediately following the C helix of IL-21 (O. Hamming, et al., Crystal Structure of Interleukin-21 Receptor (IL-21R) Bound to IL-21 Reveals That Sugar Chain Interacting with WSXWS Motif Is Integral Part of IL-21R, 287 J. Biol. Chem. 9454-9460 (2012)).

IL-21 is a class I cytokine that has pleiotropic effects on both innate and adaptive immune responses, such as stimulation of lymphocyte proliferation, promotion of CD8+ T cell and NK cell cytotoxicity, and differentiation of B cells into plasma cells. IL-21 is secreted by activated CD4+ T cells, in particular Th17 and T follicular helper cells, as well as natural killer cells. It plays an important role in promoting the development of Th17 and T follicular helper cells by a feed-forward mechanism. Furthermore, IL-21 cooperates with other cytokines to increase the cytotoxicity of CD8+ T cells and promotes proliferation of CD8+ cells in the presence of antigens. IL-21 also influences antibody production by B cells.

IL-21 has various actions, including augmenting the proliferation of T cells, driving the differentiation of B cells into memory cells and terminally differentiated plasma cells, and augmenting the activity of natural killer cells. In certain human conditions and diseases it may be desirable to block the activity of IL-21. In particular, an antibody that blocks binding of IL-21 to its receptor would be desirable in treating such conditions and diseases.

Given their properties, the antibodies of the present invention are potentially highly-suited to treatment of autoimmune conditions or diseases where T cell—B cell interactions, Th17 cells, T follicular helper cells, plasma cells and activated CD8 and NK cells play a predominant pathogenic role. Diseases that readily fit this category are primary Sjögren's Syndrome (pSS), Sjögren's Syndrome (SS) and Systemic Lupus Erythematosus (SLE), for which few treatments are available and a large medical need remains worldwide. Other potential indications include Grave's disease and type 1 diabetes.

Sjögren's Syndrome is a slowly progressing systemic autoimmune disease, seen in 0.5-1.0% of the population, which predominantly affects middle-aged women, although it can occur at any age and in both men and women. Primary Sjögren's syndrome (pSS) and Sjögren's Syndrome (SS) are characterized by chronic inflammation of the exocrine glands, in particular the salivary and lacrimal glands. The main features of pSS are oral and ocular dryness ("Sicca Syndrome") and the histological hallmark is focal lymphocytic infiltration of the exocrine glands, which may be determined by minor labial salivary gland biopsy. Sicca features affect the quality of life and cause local complications in the mucosa involved. Severe dry mouth is an unpleasant and disabling condition. However, extra-glandular manifestations occur in many patients and may involve almost any organ. There are currently no disease-modifying agents approved to treat pSS and SS. Medications address symptoms and provide supportive therapy. There is a need for more efficacious therapies with better safety profiles for patients with pSS and SS. Pharmacological intervention with the antibodies of the present invention may affect several aspects of the dysregulated immune system that appear causally related to pSS and SS pathogenesis and could thus provide significant clinical benefit to patients. This therapy also may reduce the need for chronic (non-specific) immunosuppressive agents, providing an improvement in quality of life for pSS and SS patients.

Treatment and Administration

The terms "treatment," "treating" or "to treat" and the like include restraining, slowing, stopping, or reversing the progression or severity of an existing symptom, condition, disease, or disorder in a patient. The term "patient" refers to a human. The term "effective amount" refers to the amount or dose of an antibody of the invention which, upon single or multiple dose administration to the patient, provides the desired effect in the patient. An effective amount can be readily determined by the attending diagnostician or health care professional, as one skilled in the art, by using known techniques and by observing results. In determining the effective amount for a patient, a number of factors may be considered, including, the patient's size, age, and general health; the specific disease or disorder involved; the severity of the disease, condition, or disorder; the response of the individual patient; the mode of administration; the bioavailability characteristics of the preparation administered; the dose regimen selected; the use of concomitant medication; and other relevant factors.

The antibodies of the invention are intended for parenteral administration to humans to treat autoimmune conditions. Subcutaneous and intravenous routes are preferred. The antibodies may be formulated into aqueous-based pharmaceutical solutions prior to administration. A loading intravenous dose may be administered by a health professional. Generally, administration is expected to occur by subcutaneous injection, either self-administered by the patient or by another person, such as a health care professional. For subcutaneous injections, an auto-injector or a pre-filled syringe may be used. Doses may be either fixed—that is, the same mass of active antibody for every patient—or may be based on body weight (mass). On a body weight (mass) basis, doses will preferably be in the range of 0.01 to 30 mg antibody per kilogram of body weight (mass) of the patient. More preferably, the dose will be in the range of 0.1 to 20 mg antibody per kilogram of body weight (mass) of the patient. Frequency of dosing is expected to be weekly or less frequently, depending on actual pharmacokinetics and pharmacodynamics in humans. Duration of treatment will vary depending on many factors and it will be determined by the patient's diagnostician or treating health care provider, based on experience and skill in the art. Frequency and duration of treatment may vary by indication.

Structure of the Antibodies of the Invention

The antibodies of the invention have typical tertiary and quaternary structure for a full-length human IgG antibody. When biosynthesized in a suitable mammalian host cell, the antibodies of the invention will be secreted as molecules consisting of two heavy chains and two light chains, which chains are covalently bound together by intra-chain and inter-chain disulfide bonds in the usual manner, with the heavy chains bound to each other and one light chain bound to each of the heavy chains. The positions of the intra-chain and inter-chain disulfide bonds are well-known.

Each heavy chain contains four domains: from N- to C-terminus, heavy chain variable domain, IgG CH1, IgG CH2, and IgG CH3 domains. A hinge region between CH1 and CH2 contains an inter-chain disulfide bond or bonds that join the two heavy chains. Each light chain contains two domains: from N- to C-terminus, light chain variable domain and a light chain constant domain (CL) domain. It is preferred that the heavy constant domains be human IgG4 or variants thereof. It is preferred that the light constant domain be human kappa. The variable regions together are responsible for the functional properties of binding to human IL-21 and neutralizing human IL-21 activity. The amino acid sequences of the variable regions of the antibodies of the invention are provided in SEQ ID NO:1 and SEQ ID NO:2. The constant domains of one antibody of the invention, Ab327, are given within SEQ ID NO:3 and SEQ ID NO:4. The N-linked glycosylation site at Asn294 of SEQ ID NO:3 may be glycosylated.

The amino acid sequence of the heavy chain (HC) of the antibodies consists of the heavy chain variable domain of the present invention, SEQ ID NO:1, fused at its C-terminus to appropriate human heavy chain constant domains (CH1, CH2, and CH3) or structurally-similar variants of human heavy chain constant domains that may have a well-known mutation or mutations for improving stability or reducing effector functions. Variants of human IgG4 constant domains that have mutations related to stability and/or reduced effector function, are preferred. SEQ ID NO:3 provides the amino acid sequence of the heavy chain of Ab327.

The amino acid sequence of the light chain (LC) consists of the light chain variable domain of the present invention, SEQ ID NO:2, fused at its C-terminus to an appropriate human light chain constant domain (CL) or a structurally-similar variant thereof. Human kappa light chain constant domain is preferred. SEQ ID NO:4 provides the amino acid sequence of the light chain of Ab327. For expressing Ab327, the DNA sequences given by SEQ ID NO:5 and SEQ ID NO:6 may be used for the HC and LC, respectively.

CDRs L1, L3, and H2 were assigned according to the Kabat convention and CDRs L2, H1, and H3 were assigned according to the North convention. Kabat E A, et al., *Sequences of Proteins of Immunological Interest*, Fifth Edition, U.S. Department of Health and Human Services, NIH Publication No. 91-3242 (1991); North B, et al, J Mol Biol 2011 Feb. 18; 406(2): 228-256.

Production of the Antibodies of the Invention

The antibodies of the present invention can be biosynthesized, purified, and formulated for administration by well-known methods. An appropriate host cell, such as HEK 293 or CHO, is either transiently or stably transfected with an expression system for secreting antibodies using a predetermined HC:LC vector ratio if two vectors are used, or a single vector system encoding both heavy chain and light chain. Vectors suitable for expression and secretion of antibodies from these commonly-used host cells are well-known.

Following expression and secretion of the antibody, the medium is clarified to remove cells and the clarified media is purified using any of many commonly-used techniques. For example, the medium may be applied to a Protein A column that has been equilibrated with a buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium citrate buffer pH 2.5). Antibody fractions are detected, such as by SDS-PAGE, and then are pooled. Further purification is optional, depending on the intended use. The antibody may be concentrated and/or sterile filtered using common techniques. Other materials than the antibody, such as host cell and growth medium components, and soluble aggregates and multimers of the antibody, may be effectively reduced or removed by common techniques, including size exclusion, hydrophobic interaction, cation exchange, anion exchange, affinity, or hydroxyapatite chromatography. The purity of the antibody after these chromatography steps is typically greater than 95%. The product may be stored at 4° C. frozen at −70° C. or may be lyophilized.

Ab327 used in the studies described herein was expressed either transiently in HEK293 cells after co-transfection of separate heavy chain and light chain expression DNA vectors that incorporated the DNA sequences of SEQ ID NO:5 and SEQ ID NO:6, respectively, or was expressed stably in CHO cells after transfection of a single DNA vector that incorporated the DNA sequences of both SEQ ID NO:5 and SEQ ID NO:6, which encode the heavy chain and light chain, respectively. Medium harvested from either a 5-day HEK293 culture or a 14-day CHO bulk culture were clarified and the resulting crude supernatant purified by Protein A chromatography. Ab327 bound to Protein A resin and was eluted using low pH buffer. The eluted antibody was further purified using either preparative size-exclusion chromatography (SEC), for material produced from transient transfection of HEK293, or using multimodal anion-exchange chromatography (Capto Adhere® GE Healthcare Life Sciences) as a polishing step for material produced from stable transfection of CHO. The final purity of Ab327 was evaluated by SDS-PAGE, analytical SEC-HPLC, and LC/MS analysis. Endotoxin levels were shown to be <1 EU/mg using Endosafe-PTS analysis. Purified Ab327 was stored in PBS (phosphate-buffered saline), pH 7.2 at 4° C.

Pharmaceutical Compositions of the Antibodies of the Present Invention

The purified antibody may be formulated into pharmaceutical compositions according to well-known methods for formulating proteins and antibodies for parenteral administration, particularly for subcutaneous or intravenous administration. The antibody may be lyophilized, together with appropriate pharmaceutically-acceptable excipients, and then later reconstituted with a water-based diluent prior to use. Alternatively, the antibody may be formulated in an aqueous solution and stored for up to 1 to 3 years prior to use. In either case, the stored form and the injected form of the pharmaceutical compositions of the antibody will likely contain a pharmaceutically-acceptable excipient or excipients, which are ingredients other than the antibody. Whether an ingredient is pharmaceutically-acceptable depends on its effect on the safety and effectiveness or on the safety, purity, and potency of the pharmaceutical composition. If an ingredient is judged to have a sufficiently unfavorable effect on safety or effectiveness (or on safety, purity, or potency) to warrant it not being used in a composition for administration to humans, then it is not pharmaceutically-acceptable to be used in a pharmaceutical composition of the antibody.

A solution composition of the antibody will typically be water-based and it may contain, in addition to water, excipients such as a buffering system, a preservative if intended for multiple uses, a chelating agent, a tonicity agent for adjusting the tonicity of the composition to approximate that of human tissue, and/or a solubilizing or stabilizing agent or agents, such as a detergent, a surfactant, or the like. Achieving suitably-stable formulations for long-term storage in solution can be quite challenging. Solubility and chemical and physical stability may be improved using design-of-experiment procedures by varying, for example, pH, the inclusion (or not) of various excipients, and the type and the concentration of excipients. A source for general information about formulating drugs is Remington: The Science and Practice of Pharmacy. W. Wang, et al., Antibody Structure, Instability, and Formulation, 96 J. Pharm. Sci. 1-26 (2007) is a helpful general source on formulating antibodies.

Various preferred features and embodiments of the present invention will now be described only by way of non-limiting Example and Assays with reference to the accompanying Figures.

Example 1

Antibody Generation, Engineering, and Humanization to Obtain Ab327

A mouse anti-human IL-21 antibody, 15H12, was isolated following mouse footpad immunizations and the cloning of anti-IL-21 variable regions. Balb/c mice were immunized using standard immunization procedures with human IL-21 obtained commercially. Three to five days after final non-adjuvant boost, lymph nodes and/or spleens were harvested, and single-cell suspensions were generated. Antigen-specific cells were enriched by standard sorting methods using biotinlyated or fluorophore-labeled IL-21 and were co-cultured with feeder cells for two weeks prior to cloning of mouse variable domains. The antibody was identified using an anti-IL-21 capture ELISA and was shown to block and neutralize IL-21 in in vitro assays, having a $K_D$ of about 5 pM for human and cynomolgus monkey IL-21. Fab antibody fragments were captured with a goat anti-human kappa antibody and then screened for the ability to bind biotin labelled IL-21 which in turn was detected by alkaline phosphatase labelled neutravidin. The antibody was further optimized for binding to both mouse and human IL-21 to yield mouse antibody 15M2. To accomplish this the CDRs of the isolated murine VH and VL of 15H12 were randomized by mutagenesis and resulting antibodies screened for binding to human and mouse IL-21 using an ELISA. Affinity enhancing mutations were then combined to yield 15M2, which was then humanized using a framework library approach. For the framework library, twelve human VH framework germline genes (1-24, 1-46, 1-69, 2-5, 3-15, 3-23, 3-53, 3-72, 4-04, 4-39, 5-51, and 6-01) and eight human VL framework genes (A-19, A-26, A-27, B-2, B-3, L-2, L-12, and O-2) containing 15M2's CDRs were synthesized and cloned into heavy and light chain human IgG4 expression vectors. Following 293 HEK transient transfection of all 96 heavy and light chain combinations, supernatants were assayed by ELISA for binding to human IL-21 directly coated onto a plate and to biotinylated IL-21 in solution following the capture of Human IgG from supernatants with an anti-human kappa antibody. Considering developability and ELISA activity, a humanized antibody with CDRs derived from antibody 15M2, utilizing the 1-46 heavy chain human framework and O2 human light chain framework, was chosen for further optimization. Its $K_D$ for human IL-21 was about 0.5 pM.

Analysis of the humanized antibody identified a light chain CDR deamidation site (Asn92) and a heavy chain CDR isomerization site (Asp55). To remove these chemical degradation hotspots, an engineered antibody containing both heavy chain Asp55Glu and light chain Asn92His mutations was generated. These mutations caused some loss of affinity, to about 2 pM $K_D$ for human and cynomolgus monkey IL-21. It was determined that the loss of affinity was attributed to the Asp55Glu mutation. As a result, the Asp55 residue was maintained in the heavy chain along with the Asn92His mutation in the light chain. Rational engineering principles guided further affinity optimization by engineering the near neighbor Ser56 residue in the heavy chain. From this, an engineered antibody containing a Ser56Val mutation was selected that simultaneously reduced the Asp55 isomerization and improved affinity. The final antibody has an affinity of approximately 0.5 pM to both human and cynomolgus monkey IL-21. The constant region was selected to be human IgG4, with point mutations to prevent half-antibody formation (S225P) and to reduce effector functions (F231A/L232A). In silico Epivax analysis showed no discernible immunogenicity hotspots. Sequence information for the final engineered humanized antibody ("Ab327") is shown in Table 1 below.

TABLE 1

| SEQ ID NO: | Identity | Length | Amino Acid Sequence |
|---|---|---|---|
| 1 | Heavy Chain Variable Domain | 117 | QVQLVQSGAEVKKPGASVKVSCKASGY TFTDYWMHWVRQAPGQGLEWMGLIDTS DVYTIYNQKFKGRVTMTRDTSTSTVYM ELSSLRSEDTAVYYCARYGPLAMDYWG QGTLVTVSS |
| 2 | Light Chain Variable Domain | 106 | DIQMTQSPSSLSASVGDRVTITCRASQ DISNYLNWYQQKPGKAPKLLIYYTSRL HSGVPSRFSGSGSGTDFTLTISSLQPE DFATYYCQQFHTLRTFGGGTKVEIK |
| 3 | Heavy Chain | 443 | QVQLVQSGAEVKKPGASVKVSCKASGY TFTDYWMHWVRQAPGQGLEWMGLIDTS DVYTIYNQKFKGRVTMTRDTSTSTVYM ELSSLRSEDTAVYYCARYGPLAMDYWG |

TABLE 1-continued

| SEQ ID NO: | Identity | Length | Amino Acid Sequence |
|---|---|---|---|
| | | | QGTLVTVSSASTKGPSVFPLAPCSRST SESTAALGCLVKDYFPEPVTVSWNSGA LTSGVHTFPAVLQSSGLYSLSSVVTVP SSSLGTKTYTCNVDHKPSNTKVDKRVE SKYGPPCPPCPAPEAAGGPSVFLFPPK PKDTLMISRTPEVTCVVVDVSQEDPEV QFNWYVDGVEVHNAKTKPREEQFNSTY RVVSVLTVLHQDWLNGKEYKCKVSNKG LPSSIEKTISKAKGQPREPQVYTLPPS QEEMTKNQVSLTCLVKGFYPSDIAVEW ESNGQPENNYKTTPPVLDSDGSFFLYS RLTVDKSRWQEGNVFSCSVMHEALHNH YTQKSLSLSLG |
| 4 | Light Chain | 213 | DIQMTQSPSSLSASVGDRVTITCRASQ DISNYLNWYQQKPGKAPKLLIYYTSRL HSGVPSRFSGSGSGTDFTLTISSLQPE DFATYYCQQFHTLRTFGGGTKVEIKRT VAAPSVFIFPPSDEQLKSGTASVVCLL NNFYPREAKVQWKVDNALQSGNSQESV TEQDSKDSTYSLSSTLTLSKADYEKHK VYACEVTHQGLSSPVTKSFNRGEC |

Solubility and Stability Characteristics of Ab327

Physicochemical properties of Ab327 relating to solubility and stability were assessed in both 10 mM citrate, pH 6 (C6) and 10 mM citrate, pH 6+150 mM NaCl (C6N) formulations. For the C6 formulation, solubility was ≥122.9 mg/mL and solubility in the C6N formulation was ≥130.9 mg/mL. Viscosity of Ab327 at 100 mg/mL in 10 mM citrate, 150 mM NaCl, 0.02% Tween80, pH6 formulation (C6NT) was determined to be 5.8 cP.

After 4 weeks at 25° C. in 10 mM citrate, pH 6 buffer, the changes in chemical and physical heterogeneity were low for Ab327, with less than 5% change in main peak area observed by analytical cation exchange chromatography (CEX). Under the same conditions, <0.5% high-molecular-weight (HMW) aggregate growth was observed by analytical size exclusion chromatography (SEC). Citrate, pH 6 stability samples showed no loss of bioactivity in a cell-based assay after 4 weeks at 40° C.

The antibody was analyzed after 4 weeks at 4° C., 25° C., and 40° C. in C6 by peptide mapping LC-MS for characterization of CDR chemical degradation hotspots. LC-MS analysis showed no significant isomerization of the heavy chain CDR residue Asp55 at 40° C. relative to the 4° C. control sample. Other common CDR degradations growing more than 0.5% after 4 weeks at 25° C. relative to 4° C. control sample were identified and collectively across all 6 CDRs totaled less than 5%.

The physical stability of Ab327 was assessed with a 1 mg/mL fast freeze-thaw study and a 50 mg/mL slow freeze-thaw study in C6. During both studies, the presence of Tween80 reduced the formation of 10 micron size particles. In the high concentration study, the presence of 150 mM NaCl salt reduced HMW aggregate formation. For the low concentration study, HMW aggregate was 0.7% in the presence of salt and Tween80. In conclusion, Ab327 appeared from these tests to have good solution properties, including viscosity, solubility, and stability, to proceed into human studies.

Functional Properties of Ab327

Binding of Ab327 to Human IL-21 and other Human Common-gamma Chain Receptor Family Members by ELISA The objective of this study was to determine the binding specificity of Ab327 to human IL-21 as compared with the other members of the common-gamma (γc) chain receptor cytokines. The cytokine receptor γc-chain family consists of six members, IL-2, IL-4, IL-7, IL-9, IL-15, and IL-21. All members of this family signal through receptor complexes that contain the γc subunit. The specificity of Ab327 for binding to other human γc chain cytokine family members was determined using an ELISA. Briefly, Ab327 was captured on an ELISA plate coated with goat anti-human kappa IgG. Cytokines labeled with biotin titrated from 100 nM-780 pM were then added to the plate for 1 hour at 37° C. and any bound cytokine was detected using Neutravidin labeled with alkaline phosphatase. Commercially available mouse monoclonal antibody to IL-2 and goat polyclonal antibodies to IL-4, IL-7, IL-9 and IL-15 captured with donkey anti-goat IgG gave positive signals after binding the biotinylated cytokines and detection with Neutravidin. However, no detectable signal was observed for Ab327, except with human IL-21 (see Table 2 below, which shows the binding of Ab327 and other ligands that bind human common-gamma chain receptor by ELISA as shown as Optical Density (OD) measurement at 560 nm. See also FIG. 1). These results indicate that Ab327 is specific to IL-21 and does not bind other human γc chain receptor family cytokines.

TABLE 2

| Protein | | Protein conc. (nM) | | | | | | | |
|---|---|---|---|---|---|---|---|---|---|
| | | 100 | 33 | 11 | 3.7 | 1.2 | 0.41 | 0.14 | 0.05 |
| IL-2 | Positive control | 1.25 | 0.59 | 0.24 | 0.13 | 0.10 | 0.08 | 0.09 | 0.09 |
| | Ab327 | 0.07 | 0.07 | 0.07 | 0.08 | 0.08 | 0.08 | 0.09 | 0.09 |
| IL-4 | Positive control | 1.78 | 1.75 | 1.63 | 1.44 | 1.18 | 0.92 | 0.54 | 0.27 |
| | Ab327 | 0.08 | 0.07 | 0.07 | 0.07 | 0.07 | 0.07 | 0.07 | 0.07 |
| IL-7 | Positive control | 2.88 | 2.85 | 2.73 | 1.96 | 0.92 | 0.37 | 0.18 | 0.12 |
| | Ab327 | 0.07 | 0.07 | 0.07 | 0.07 | 0.08 | 0.07 | 0.08 | 0.08 |
| IL-9 | Positive control | 1.70 | 1.21 | 0.68 | 0.34 | 0.18 | 0.12 | 0.10 | 0.09 |
| | Ab327 | 0.07 | 0.07 | 0.07 | 0.11 | 0.07 | 0.07 | 0.07 | 0.07 |
| IL-15 | Positive control | 1.70 | 1.49 | 1.21 | 0.87 | 0.44 | 0.21 | 0.14 | 0.09 |
| | Ab327 | 0.07 | 0.07 | 0.07 | 0.07 | 0.07 | 0.11 | 0.08 | 0.07 |
| IL-21 | hIgG4 | 0.06 | 0.06 | 0.06 | 0.06 | 0.06 | 0.06 | 0.06 | 0.06 |
| | Ab327 | 0.81 | 0.81 | 0.76 | 0.76 | 0.71 | 0.52 | 0.34 | 0.20 |

Binding Affinity of Ab327 for Human, Cynomolgus Monkey, Mouse, Rat, and Rabbit IL-21

Ab327 is an engineered, humanized monoclonal IgG4 antibody that binds and neutralizes human IL-21. The purpose of this study was to determine the binding affinity of Ab327 for human, cynomolgus monkey, mouse, rat, and rabbit IL-21 (the sequences are given below). The apparent binding affinity ($K_D$) of Ab327 to these various IL-21 species was determined using a KinExA 3000 instrument at 37° C. KinExA solution equilibrium binding experiments were performed using a fixed antibody concentration protocol and 2-fold serial dilutions of IL-21. Samples were equilibrated at 37° C. for 6-36 hours prior to analysis. Free antibody in the equilibrated samples was detected using a Dylight 649-conjugated anti-human IgG Fc polyclonal antibody. The resulting percent free antibody versus antigen concentration data were fit to an "affinity, standard" binding model using the KinExA Pro software, and the best fit binding affinity value ($K_D$) was determined.

The average $K_D$ from three independent experiments along with the standard deviation (human, cynomolgus monkey, mouse, and rat) or from a single determination (rabbit IL-21) is summarized in Table 3 below (apparent solution equilibrium binding affinity ($K_D$) of Ab327).

TABLE 3

| IL-21 Species | Number of Independent Determinations | Apparent Solution Equilibrium Binding Affinity of Ab327 at 37° C. $K_D$ (M) |
|---|---|---|
| Human | 3 | $0.8 \pm 0.5 \times 10^{-12}$ |
| Cynomolgous Monkey | 3 | $0.3 \pm 0.1 \times 10^{-12}$ |
| Mouse | 3 | $2.4 \pm 1.3 \times 10^{-7}$ |
| Rat | 3 | $2.3 \pm 0.2 \times 10^{-7}$ |
| Rabbit | 1 | $>2 \times 10^{-7}$ |

Ab327 bound to human and cynomolgus monkey IL-21 with an average (n=3) affinity of $0.8 \pm 0.5 \times 10^{-12}$ M and $0.3 \pm 0.1 \times 10^{-12}$ M, respectively, at 37° C. Ab327 bound to mouse, rat, and rabbit IL-21 with an affinity of $2.4 \pm 1.3 \times 10^{-7}$ M, $2.3 \pm 0.2 \times 10^{-7}$ M, and $>2 \times 10^{-7}$ M, respectively. The binding to rabbit IL-21 was estimated based on a binding signal that was less than what was observed for equivalent samples of mouse and rat IL-21. Based on these results, Ab327 has approximately picomolar level affinity for human and cynomolgus monkey IL-21 but a relatively weak affinity for mouse, rat, and rabbit IL-21.

Ab327 inhibited Human and Cynomolgus Monkey IL-21 in an IM9 pan-STAT-Luciferase Reporter Assay In Vitro.

IL-21 activates the JAK-family protein tyrosine kinases which mediate the IL-21-dependent activation of Signal Transducer and Activator of Transcription (STAT). The ability of IL-21 to activate the STAT pathway was assessed using IM9 cells. IM9 cells, which are an EBV-transformed B lymphoblastoid cell line derived from the blood of a patient with multiple myeloma and which naturally express the IL-21 receptor (IL-21R) and its co-receptor (γc), were stably transfected with a pan-STAT-luciferase reporter construct. Using an IM9-panSTAT-luciferase reporter assay, the goal of this experiment was to determine whether Ab327 could inhibit the IL-21-dependent activation of STAT.

IM9-panSTAT-luciferase cells (IM9 cells subclone 1B 10/3G2 with pan-STAT luciferase reporter) were routinely cultured in medium (RPMI1640, 10% FBS, 1×pen/strep, 100 μg/mL Zeocin for selection of the pan-STAT-luciferase reporter) in flasks. For the assay, cells were seeded at 50,000 cells/50 μL/well in TC-treated plates and incubated overnight at 37° C. Then, the cells were treated with Ab327 in the presence of recombinant IL-21 proteins from different species. A dose range of Ab327 from 0 to 6670 pM was evaluated (final concentration was based on MW of Ab327=150 kDa). Recombinant IL-21 from different species were added to each well to a final concentration of 66.67 pM (based on MW=15 kDa). A human IL-21R:Fc chimera (R&D Systems, cat #991-R2) was used as positive control and human IgG4 was used as a negative control. A dose range for the positive and negative control from 0 to 47520 pM was evaluated. Testing was carried out in triplicate. The 96-well plates were placed in a tissue culture incubator (37° C., 95% relative humidity, 5% $CO_2$) for 4 hours. 100 μL/well of One-Glo Luciferase solution was added to stop the assay. A luminometer (Perkin Elmer Victor3) was used to read the plates.

Results are expressed as IC50 (the half maximal inhibitory concentration) and calculated using a 4-parameter sigmoidal fit of the data (Sigma plot). The average IC50s from three independent experiments and the standard deviations are reported in Table 4 below.

TABLE 4

| IC50 (pM) | Human IL-21 | Cyno IL-21 | Mouse IL-21 | Rat IL-21 | Rabbit IL-21 |
|---|---|---|---|---|---|
| Ab327 | 46.7 ± 2.4 | 48.3 ± 5.9 | N.N.D. | N.N.D. | N.N.D. |
| hIL21R-Fc | 271 ± 15.6 | 3922 ± 525 | 3533 ± 543 | N.N.D. | 321 ± 76.2 |

Within the range tested, Ab327 completely inhibited human and cynomolgus monkey IL-21-induced STAT activity in a dose-dependent manner. The inhibition by Ab327 was greater than that observed with the positive control (hIL-21R: Fc), with Ab327 having an IC50 of 46.7±2.4 versus 271±15.6 for the positive control. The isotype control antibody (hIgG4) did not inhibit pan-STAT activity (data not shown). In conclusion, Ab327 effectively neutralized human and cynomolgus monkey IL-21 activity in vitro, but it did not neutralize mouse, rat, or rabbit IL-21 (sequences given above) under these conditions (N.N.D.=neutralization not detected).

Ab327 Neutralized Human IL-21-Induced Proliferation of Primary Human B Cells In Vitro.

The primary function of B cells is to produce antibodies that neutralize and clear pathogens. Antibody-producing B cells are generated from naïve B cells during germinal center (GC) reactions. The GCs are established when B cells encounter specific antigens and receive instructive signals from T follicular helper cells for growth, survival, selection, and differentiation. Among those signals, B cells are stimulated by CD40 and numerous cytokines, with IL-21 being a key factor in promoting proliferation, isotype switching, plasma cell differentiation, and secretion of antibodies. The goal was to determine whether Ab327 was able to inhibit IL-21-induced proliferation of primary human B cells.

Buffy coats from five healthy donors were obtained from Indiana Blood Center. PBMCs were isolated from buffy coats by Ficoll-Paque gradient separation and CD19+ B cells were positively selected with anti-CD19 magnetic beads (Miltenyi Biotec). The purity of the recovered population was typically >90%. To assess proliferative responses of cultured cells, purified CD19+ cells were cultured at 0.5 million cells/mL (0.1 million cells/well) in 96-well flat-bottom culture plates with appropriate stimulators (RPMI-1640/10% FBS containing 1 mM sodium pyruvate, non-essential amino acids, 10 mM HEPES pH 7.0, 100 U/mL penicillin and 100 µg/mL streptomycin) for 5 days at 37° C. and 5% $CO_2$. Isolated B cells were incubated with a combination of human IL-21 at 3.33 nM (based on MW=15 k Da) and 2 µg/mL anti-human CD40 (BD Pharmingen). A dose range of Ab327 (from 0.1 nM to 26.7 nM), human IL-21R:Fc chimera (from 0.1 nM to 213.3 nM, R&D Systems) or human IgG4 (from 0.1 nM to 26.7 nM) were evaluated. All stimuli and treatments were added at culture initiation. After 5 days of culture, [methyl-3H] Thymidine uptake was measured using a liquid scintillation counter.

Figure 2:
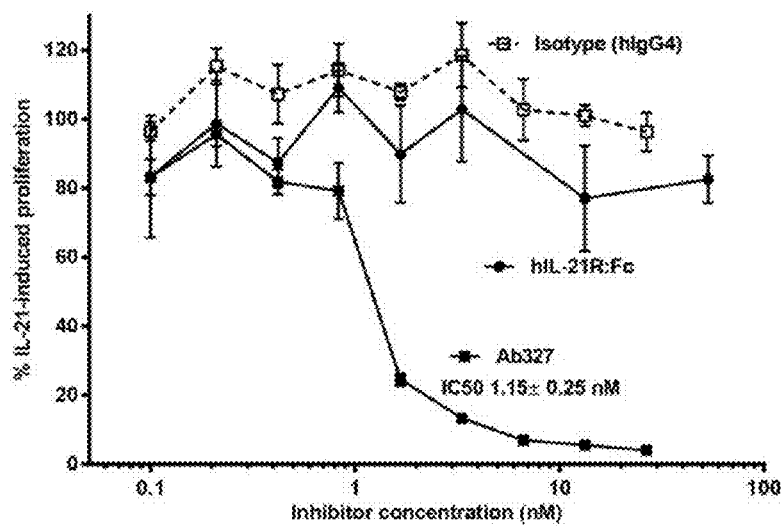
FIG. 2. Ab327 is shown to neutralize human IL-21-induced proliferation of primary human B cells in vitro.

Results are expressed as percent of maximum proliferation, with IL-21-mediated stimulation in the absence of antibody being 100%. The concentration where 50% of the IL-21-induced response was inhibited (IC50) by Ab327 was calculated using a 4-parameter sigmoidal fit of the data. Ab327 inhibited IL-21-induced proliferation of primary human B cells in a dose-dependent manner. This inhibition was much greater than that observed with the positive control, a human IL-21R-Fc construct, which, at the highest concentration used (26.7 nM), was not able to completely inhibit IL-21-induced proliferation (See FIG. 2). The calculated IC50 for Ab327 was 1.15±0.25 nM (average of 5 independent experiments±SD). The negative control antibody (isotype control hIgG4) did not inhibit IL-21-induced proliferation of primary B cells. Table 5 shows Ab327 is able to neutralize human IL-21-induced proliferation of primary human B cells in vitro. The numbers show the percentage of proliferating human B cells±SDEV. In conclusion, Ab327 inhibited IL-21-induced proliferation of primary human B cells in vitro.

TABLE 5

| IC* | Values** hIgG4 Isotype | SDEV | Values** huIL-21 R: Fc | SDEV | Values** Ab327 | SDEV |
|---|---|---|---|---|---|---|
| 0 | 100 | — | 100 | — | 100 | — |
| 0.1 | 96 | 5.34 | 83 | 15.8 | 83 | 10.4 |
| 0.21 | 115 | 10.3 | 99 | 10.8 | 96 | 6.77 |
| 0.42 | 107 | 17.1 | 87 | 6.43 | 82 | 7.21 |
| 0.83 | 114 | 15.3 | 109 | 6.33 | 79 | 16.2 |
| 1.67 | 108 | 4.78 | 90 | 12.6 | 25 | 3.68 |
| 3.33 | 119 | 18.7 | 103 | 13.7 | 13 | 2.38 |
| 6.67 | 103 | 17.9 | — | — | 6.9 | 1.59 |
| 13.3 | — | — | 77 | 13.8 | — | — |
| 13.3 | 101 | 6.21 | — | — | 5.5 | 1.47 |
| 26.7 | 96 | 11.2 | — | — | 4.0 | 1.34 |
| 53.3 | — | — | 83 | 6.2 | — | — |

*inhibitor concentration (nM)
**% weight change for each treatment

Ab327 Neutralized Human IL-21-Induced Plasma Cell Differentiation of Primary Human B Cells In Vitro.

B cell differentiation into plasmablasts is regulated by the integration of signals provided by antigen and T cells (CD40-CD40L interaction and production of cytokines). One of the cytokines important for human B cell differentiation is IL-21, which induces plasma cell generation and antibody secretion from activated naïve and memory B cells. It has been shown that IL-21 induces CD25 (IL-2R) expression on activated B cells, sensitizing those cells to the differentiation-promoting effects of IL-2, thereby enabling co-operative interplay between IL-2 and IL-21 to amplify plasmablast generation and antibody secretion. The goal was to determine whether Ab327 was able to inhibit IL-21-induced differentiation of primary human B cells into plasma cells in vitro.

Buffy coats were obtained as described above. Purified B cells were cultured at 0.75 million cells/mL (0.15 million cells/well) in 96-well flat-bottom culture plates with appropriate stimulators (RPMI-1640/10% FBS containing 1 mM sodium pyruvate, non-essential amino acids, 10 mM HEPES pH 7.0, 100 U/mL penicillin and 100 µg/mL streptomycin) for 6 days at 37° C. and 5% $CO_2$. Isolated B cells were incubated with a combination of 3.33 nM human IL-21, 1 µg/mL anti-human CD40 (BD Pharmingen), 100 U/mL of human IL-2 (Proleukin, Hanna's Pharmaceutical Supply Co.) and/or 26.7 nM Ab327 or 26.7 nM of a human IgG4 antibody (negative control). Six days after culture, cells were washed with staining buffer (2% FBS/PBS) and incubated with antibodies specific for human CD38, IgD, CD19, CD27 (all from BD Biosciences) for 40 minutes at 4° C. Five-color flow cytometry analysis was performed using an FC-500 flow cytometer (Beckman Coulter). Plasma cells were identified as cells expressing high levels of CD38 and low levels of IgD (See Table 6 below).

Since there is a high variability amongst donors, the results shown below are expressed as fold increase of the relative number of plasma cells (CD38 high+IgD low cells) induced by addition of IL-21, where the value for plasma cells derived from each donor in medium+anti-CD40+ IL-2 is set to equal one (1). Data are shown as "fold increase" for effects on primary human B cells from five healthy donors.

TABLE 6

| Medium + anti-CD40 + IL-2 | Medium + anti-CD40 + IL-2 + IL-21 | Medium + anti-CD40 + IL-2 + IL-21 + IgG4 Isotype | Medium + anti-CD40 + IL-2 + IL-21 + Ab327 |
|---|---|---|---|
| 1 | 176 | 174 | 11.7 |
| 1 | 114 | 108 | 3.38 |
| 1 | 47 | 47 | 7.81 |
| 1 | 68 | 66 | 6.87 |
| 1 | 22 | 23 | 3.64 |

Fresh B cells cultured with the combination of anti-CD40 and IL-2 contained few CD38 high/IgD low plasma cells. In contrast, co-stimulation of purified B cells with anti-CD40 and IL-2 in the presence of IL-21 resulted in substantial differentiation into plasma cells. The negative control antibody (Isotype hIgG4) was not able to inhibit IL-21 activity. Ab327 inhibited IL-21-induced plasma cell differentiation of primary human B cells (n=5 donors, p=0.008, Unpaired t-Test Ab327 vs. IgG4 isotype antibody). In conclusion, Ab327 inhibited human IL-21-induced plasma cell differentiation in vitro.

Ab327 Neutralized Human IL-21 Activity in Mice.

Injection of IL-21 into mice leads to a rapid and transient expansion of several cell types in the spleen (including subpopulations of B and T cells) clearly identified using specific markers. The goal of this experiment was to investigate whether Ab327 was able to inhibit the biological activity of human IL-21 in mice.

Eight to ten weeks old female C57Bl6 mice (n=5 per group) were injected intraperitoneally (i.p.) with either Ab327 (1 mg/mouse) or isotype (hIgG4, 1 mg/mouse) control antibody on day 1. On days 2 and 3 mice received i.p. injection of 50 µg of recombinant human IL-21 per mouse per day or PBS. On day 4, a cell suspension of spleen cells was prepared and the total number of cells was determined after lysing the red blood cells. The relative percentage of IL-21-responsive cells was determined using the cell surface markers Gr-1 and Sca-1 by flow cytometry. The total number of IL-21-responsive cells per spleen was calculated by multiplying the percentage of IL-21-responsive cells (Gr-1lowSca-1+ cells) by the total number of cells in the spleen. Results in Table 7 below are shown as total number of IL-21 responsive cells ($\times 10^6$) in the spleen of each of five mice.

TABLE 7

| Number of hIL-21 responsive spleen cells ($\times 10^6$) | | |
|---|---|---|
| PBS + IgG4 isotype | hIL-21 + IgG4 isotype | hIL-21 + Ab327 |
| 1.72 | 9.12 | 2.26 |
| 1.73 | 9.19 | 2.32 |
| 2.59 | 9.23 | 3.49 |
| 2.64 | 11.78 | 2.34 |
| 2.36 | 12.27 | 5.25 |

Injection of human IL-21 caused an increase of IL-21 responsive cells. The presence of Ab327 reduced the number of those cells (p<0.0001, Unpaired t-Test Ab327+ IL-21 vs. IgG4+ IL-21 and IgG4+ PBS vs. IgG4+ IL-21) relative to animals that received a negative control antibody. Exposure to Ab327 and negative control antibodies within each group was confirmed by quantitative ELISA. It is concluded that Ab327 effectively neutralized the biological activity of human IL-21 in vivo.

Ab327 Demonstrated Efficacy in an In Vivo Model of Human T Cell Activation in NGS Mice.

It has been previously shown that neutralizing human IL-21 prevents the progression of disease in a human T-cell activation model in which human peripheral blood mononuclear cells (PBMCs) are engrafted into severely immunocompromised NSG mice (NOD-scid IL-2Rγ null; Hippen K L, et al. Blocking IL-21 signaling ameliorates xenogeneic GVHD induced by human lymphocytes. Blood 2012; 119: 619). NSG mice lack T, B and NK cells, and also have reduced function of macrophages and dendritic cells. Transplantation of human PBMCs results in overt human T-cell activation and their infiltration into mouse skin, liver, intestine, lungs and kidneys. This is accompanied by a wasting syndrome that eventually leads to death (Hippen, 2012). The advantage of this model is that the disease is driven by human immune cells and human cytokines, thus allowing for in vivo interrogation of antibodies that lack cross-reactivity to other species. The purpose of this study was to demonstrate in vivo efficacy and disease modifying activity of Ab327 in the human T-cell activation model when administered in prevention mode (administered beginning at the time of engraftment) or treatment mode (administered beginning at 21 days post engraftment).

Figure 3:
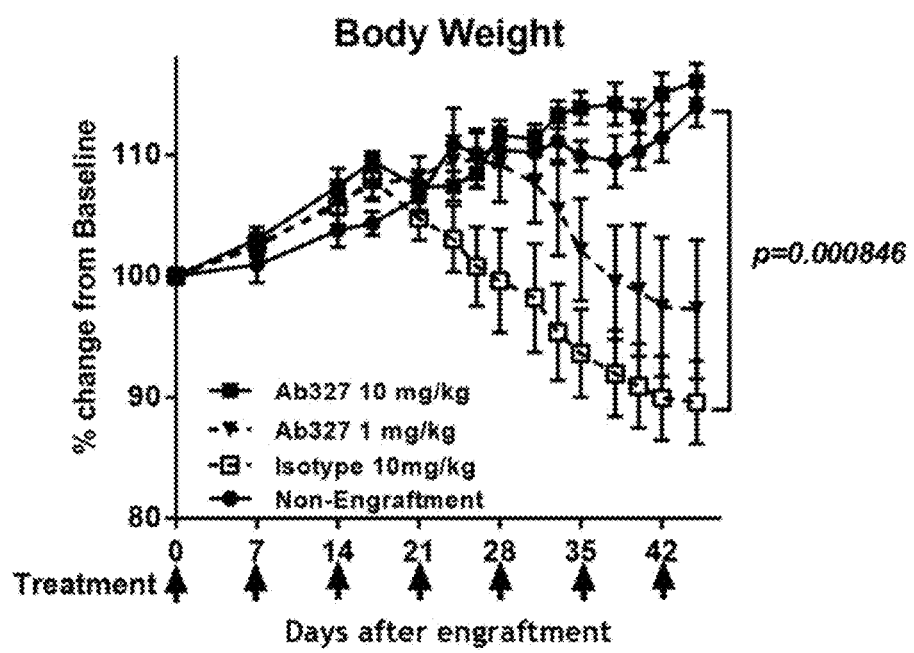
FIG. 3. Average percent of body weight change from baseline in severely immuno-compromised NSG mice (NOD-scid IL-2Rγ null) engrafted with human peripheral blood mononuclear cells (PBMCs) treated with IL-21 antibody or isotype control antibody for 42 days. Treatments occurred at points indicated by arrows. Symbols: -■- Ab327 (10 mg/kg); -▼- Ab327 (1 mg/kg); -□-; Isotype control (10 mg/kg); -●- non-engraftment.

Prior to engraftment, female NSG mice were divided into groups based on baseline measurements of body weight (n=10/group). On day 0, mice were injected intravenously with $10^7$ human PBMCs isolated from a buffy coat acquired from the San Diego Blood bank. For prevention mode (FIG. 3), mice were dosed subcutaneously with 1 or 10 mg/kg Ab327 or 10 mg/kg hIgG4 isotype control antibody at time of engraftment and once weekly thereafter. Body weight was measured and general appearance and health was monitored 2-3 times per week. On day 19, blood was obtained by tail snip and analyzed for engraftment of human CD45+ cells by flow cytometry. For treatment mode (FIG. 4), animals that did not receive any treatment were re-assigned into matched cohort groups based on the flow cytometry data and body weight. On day 21 after engraftment, mice were dosed subcutaneously with 10 mg/kg Ab327 or 10 mg/kg hIgG4 isotype control antibody, and then once weekly thereafter. Four non-engrafted mice were included as "untreated controls or non-engrafted" mice. The body weight change was calculated as a percentage of baseline weight (Day(x)weight/Day 0 weight*100). Results are shown as percent body weight change from baseline over time.

For prevention mode, mice treated with a human isotype control antibody (see FIG. 3, open squares) developed a wasting phenotype as early as 20 days after cell transfer. On day 45 post transfer, the average weight loss in the isotype control group was greater than 10% from baseline and the majority of mice were in distress, and thus the study was terminated. Treatment with 10 mg/kg/week Ab327 (FIG. 3, closed squares) initiated on the day of engraftment (prevention mode) completely abolished the wasting phenotype. Mice continued to gain weight comparable to non-engrafted mice. Their weights were statistically significantly different from the isotype control group (p=0.000846 and p<0.001 Ab327 versus isotype and non-engrafted mice versus isotype respectively, 2-way ANOVA, repeated measures). The 1 mg/kg/week dose of Ab327 (FIG. 3, closed triangles) had a partial effect, in that it appeared to slow the progression of weight loss. However, the weights of mice in this group were not statistically different from the isotype control. Table 8 shows average±SDEV percent of body weight change from baseline in severely immuno-compromised NSG mice (NOD-scid IL-2Rγ null) engrafted with human peripheral blood mononuclear cells (PBMC) treated with IL-21 antibody or isotype control antibody for 45 days. Treatment started at the same time as engraftment of PBMC. There is a significant difference between the Ab327 10 mg/kg group and the Isotype control group.

TABLE 8

| Days*** | Values*- non- engraftment | SDEV | Values*- isotype 10 mg/kg | SDEV | Values*- Ab 327 10 mg/kg | SDEV | Values*- Ab 327 1 mg/kg | SDEV |
|---|---|---|---|---|---|---|---|---|
| 0  | 100.0 | 0.0 | 100.0 | 0.0  | 100.0 | 0.0 | 100.0 | 0.0  |
| 7  | 100.9 | 3.0 | 102.7 | 2.9  | 103.1 | 3.1 | 102.5 | 2.7  |
| 14 | 103.8 | 2.8 | 105.8 | 5.0  | 107.4 | 4.6 | 106.2 | 3.4  |
| 17 | 104.4 | 1.9 | 108.0 | 4.8  | 109.5 | 2.6 | 107.5 | 4.0  |
| 21 | 106.5 | 2.7 | 104.8 | 5.8  | 107.4 | 3.9 | 108.2 | 5.1  |
| 24 | 110.8 | 6.1 | 103.1 | 8.8  | 107.4 | 3.9 | 109.5 | 6.6  |
| 26 | 110.1 | 4.1 | 100.8 | 10.4 | 108.5 | 3.6 | 109.6 | 7.3  |
| 28 | 110.4 | 2.8 | 99.6  | 13.5 | 111.7 | 3.9 | 109.2 | 9.8  |
| 31 | 110.2 | 3.7 | 98.2  | 14.2 | 111.3 | 4.1 | 107.7 | 10.4 |
| 33 | 111.2 | 3.2 | 95.4  | 12.5 | 113.4 | 3.6 | 105.5 | 11.9 |
| 35 | 109.9 | 2.5 | 93.6  | 11.5 | 113.9 | 4.3 | 102.2 | 13.4 |
| 38 | 109.5 | 4.3 | 91.9  | 11.3 | 114.2 | 5.5 | 99.5  | 15.0 |
| 40 | 110.3 | 2.9 | 90.9  | 11.1 | 113.2 | 4.4 | 98.8  | 17.2 |
| 42 | 111.4 | 4.0 | 89.9  | 11.1 | 115.2 | 5.4 | 97.5  | 18.1 |
| 45 | 114.0 | 3.3 | 89.6  | 10.9 | 116.1 | 4.5 | 97.3  | 18.1 |

**% weight change for each treatment
***days after engraftment

Figure 4:
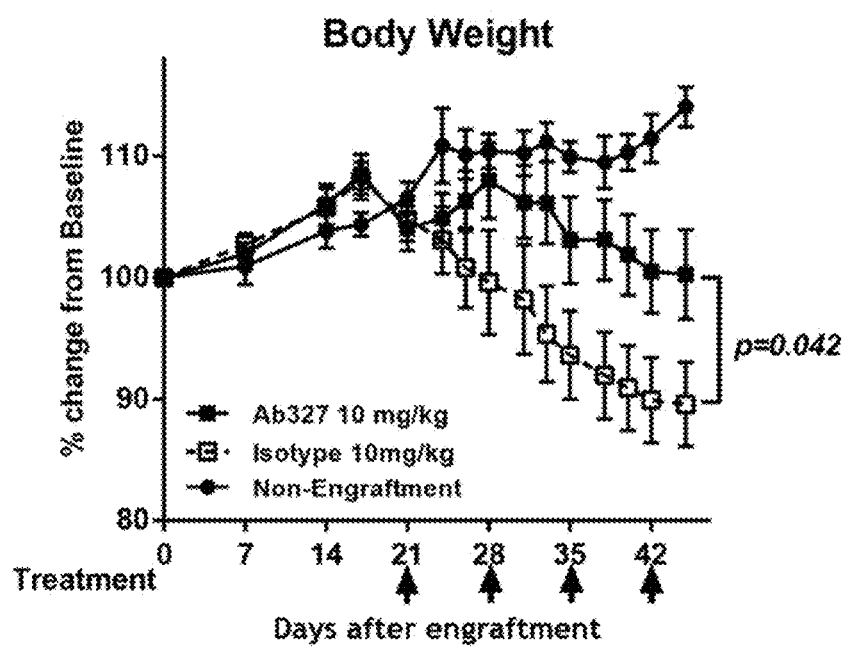
FIG. 4. Average percent of body weight change from baseline in severely immuno-compromised NSG mice (NOD-scid IL-2Rγ null) engrafted with human peripheral blood mononuclear cells (PBMCs) treated with IL-21 antibody or isotype control antibody. Treatments occurred at points indicated by arrows. Symbols: -■- Ab327 (10 mg/kg); -□-; Isotype control (10 mg/kg); -●- non-engraftment.

As noted above, human PBMCs administration resulted in a wasting disease starting approximately 20 days after engraftment. To investigate if blockade of human IL-21 was able to halt the ongoing deteriorating disease (treatment mode), mice were treated with 10 mg/kg/week Ab327 or hIgG4 isotype control starting on day 21 after engraftment. As shown in FIG. 4, mice dosed with the human IgG4 isotype control antibody (open squares) continue losing weight. On the other hand, Ab327 treatment, initiated after onset of disease (21 days post-engraftment, FIG. 4, closed squares), was effective in attenuating the wasting phenotype. The average weight in this group was statistically significantly different from the isotype control group (p=0.042, 2-way ANOVA, repeated measures). The difference in weight loss and severity of disease was not due to differences in engraftment of human cells into the mice. Peripheral human CD45+ cell numbers as well as human cells in the spleen at the end of the study were slightly higher in the Ab327 treated mice compared to isotype control treated animals. In summary, Ab327 demonstrated efficacy and disease modifying activity in a xenogeneic model of T-cell activation in vivo. Table 9 shows the average±SDEV percent of body weight change from day 21 in severely immuno-compromised NSG mice (NOD-scid IL-2Rγ null) engrafted with human peripheral blood mononuclear cells (PBMC) treated with IL-21 antibody or isotype control antibody. Treatment started at day 21. There is a significant difference between the Ab327 10 mg/kg group and the Isotype control group.

TABLE 9

| Days*** | Values** - non- engraft- ment | SDEV | Values** - isotype 10 mg/kg | SDEV | Values** - Ab327 10 mg/kg | SDEV |
|---|---|---|---|---|---|---|
| 21 | 100.0 | 0.0 | 100.0 | 0.0  | 100.0 | 0.0 |
| 24 | 104.0 | 4.7 | 98.2  | 4.1  | 100.8 | 3.5 |
| 26 | 103.4 | 1.8 | 96.0  | 6.5  | 102.1 | 4.1 |
| 28 | 103.7 | 3.0 | 94.8  | 9.7  | 103.7 | 5.3 |
| 31 | 103.5 | 2.9 | 93.5  | 10.8 | 101.9 | 4.8 |
| 33 | 104.3 | 1.3 | 90.8  | 8.9  | 101.9 | 5.8 |
| 35 | 103.2 | 1.2 | 89.1  | 8.0  | 98.9  | 7.1 |
| 38 | 102.8 | 3.8 | 87.6  | 8.0  | 99.0  | 6.7 |
| 40 | 103.5 | 2.0 | 86.6  | 8.0  | 97.8  | 6.8 |
| 42 | 104.6 | 1.8 | 85.7  | 8.1  | 96.5  | 7.4 |
| 45 | 107.0 | 1.7 | 85.3  | 8.0  | 96.2  | 8.0 |

**% weight change for each treatment
***days after engraftment

Pharmacokinetics of Ab327

Pharmacokinetics of Ab327 was characterized after a single intravenous or subcutaneous 3 mg/kg dose in male cynomolgus monkeys. Serum samples were collected out to 1008 hours post-dose (6 weeks). Concentration-time profiles were generated after quantifying antibody using two ELISA methods (total human IgG or antigen capture). The total human IgG method utilizes an ELISA format to measure the concentration of anti-IL-21 antibody. Standards, controls and test samples were incubated with AffiniPure F(ab')2 Fragment Goat Anti-Human IgG (coating Ab) that had been immobilized on a microtiter plate. After incubation, a mouse anti-human IgG4-HRP (horseradish peroxidase) was added to the wells. Once unbound enzyme was washed away, Sure-Blue® TMB (tetramethylbenzidine) substrate solution was added to the wells. The color development was stopped by the addition of an acidic solution and the optical density was measured at 450 nm with wavelength correction set to 650 nm.

The antigen capture method utilizes an ELISA format to measure the concentration of anti-IL-21 antibody. Standards, controls and test samples were incubated with human IL-21-biotin that had been immobilized on a streptavidin coated microtiter plate. After incubation, a mouse anti-human IgG4-HRP (horseradish peroxidase) was added to the wells. Once the unbound enzyme was washed away, SureBlue® TMB (tetramethylbenzidine) substrate solution was added to the wells. The color development was stopped by the addition of an acidic solution and the optical density was measured at 450 nm with wavelength correction set to 650 nm. The assay range was 5-500 ng/mL.

Pharmacokinetic results (means) are provided below in Table 10 and Table 11. The number of animals in each group was 2.

TABLE 10

| | IV administration values | | | | | |
|---|---|---|---|---|---|---|
| Assay | $t_{1/2}$* (h) | $AUC_{0-t}$ (h * µg/ mL) | $AUC_{0-INF}$ (h * µg/mL) | AUC % Extrap (%) | CLss (mL/h/kg) | Vss (mL/kg) |
| Capture | 249 | 6200 | 6750 | 7.36  | 0.430 | 47.2 |
| Total   | 105 | 6170 | 6220 | 0.823 | 0.484 | 52.0 |

Abbreviations = $t_{1/2}$—half-life, $AUC_{0-t}$—area under the curve from 0 to last measurable concentration, $AUC_{0-INF}$—area under the curve from 0 to infinity, AUC % Extrapolated—Percentage of $AUC_{0-INF}$ due to extrapolation from last measurable concentration to infinity, CLss—estimate of total body clearance, Vss—estimate of volume of distribution at steady-state.
*Terminal half-lives were calculated between 72-168 hours.

TABLE 11

Subcutaneous administration values

| Assay | $t_{1/2}$* (h) | Tmax | Cmax | $AUC_{0-t}$ (h * μg/mL) | $AUC_{0-INF}$ (h * μg/mL) | AUC % Extrap (%) | CLss/F (mL/h/kg) | F % (mL/kg) |
|---|---|---|---|---|---|---|---|---|
| Capture | 51.8 | 60 | 21.6 | 4410 | 4540 | 2.45 | 0.683 | 72 |
| Total | 53.6 | 84 | 24.0 | 4620 | 4620 | 0.0276 | 0.675 | 74 |

Abbreviations = $t_{1/2}$—half-life, Tmax—time at maximal concentration, Cmax—maximal concentration, $AUC_{0-t}$—area under the curve from 0 to last measurable concentration, $AUC_{0-INF}$—area under the curve from 0 to infinity, AUC % Extrapolated—percentage of $AUC_{0-INF}$ due to extrapolation from last measurable concentration to infinity, CLss/F—clearance/bioavailability, F %—bioavailability using mean 3 mg/kg i.v. dose as reference = ($AUC_{0-INF}$ s.c./$AUC_{0-INF}$ i.v.)/(Dose-iv/Dose-s.c.) * 100.
*Terminal half-lives were calculated between 96-336 hours.

After a single intravenous or subcutaneous administration of Ab327 to male cynomolgus monkeys, concentration-time profiles were suggestive of anti-drug antibody (ADA) formation and ADA was confirmed in 4/4 monkeys. The mean terminal half-life was 105-249 hours and was calculated from the slope between 72-168 hours to avoid significant impact of ADA. Mean clearance was 0.43-0.48 ml/h/kg which falls just outside of a typical monoclonal antibody clearance range of 0.2-0.4 ml/h/kg.

After subcutaneous administration, bioavailability was 72-74% which falls in the typical range for a monoclonal antibody (50-100%). Despite ADA formation, the pharmacokinetics of Ab327 in monkeys was relatively similar to that expected for a monoclonal antibody binding a soluble ligand with clearance being slightly higher than normal.

On the basis of these studies, it is concluded that Ab327 will have pharmacokinetics in humans within the expected range for a humanized IgG4 antibody. Projected human clearance is 0.3 mL/hr/kg (0.02 L/h in a 70 kg human) based on allometric scaling of monkey clearance and bioavailability is projected to be 50-75% in humans.

Treatment with Anti-Mouse IL-21 Antibody Alleviated Lymphocytic Infiltration in Salivary Glands of NOD Mice.

Because Ab327 does not neutralize rodent IL-21, a surrogate molecule was developed for use in preclinical disease models. Antibody Ab728 is a murine IgG1 monoclonal antibody that binds specifically to mouse IL-21. The binding affinity of murine IL-21 to Ab728 is 1 pM. Ab728 was able to completely neutralize murine IL-21 in in vivo and in vitro assays.

The non-obese diabetic (NOD) mouse is widely used as a model of Sjögren's Syndrome because it spontaneously develops lymphocytic infiltration in the salivary glands. Previous work showed that local suppression of IL-21 levels in submandibular glands of NOD mice with IL-21 shRNA lentivirus could retard the development of Sjögren's Syndrome-like symptoms (Liu H, et al. Local suppression of IL-21 in submandibular glands retards the development of Sjögren's syndrome in non-obese diabetic mice. J Oral Pathol Med 2012; 41:728). The goal of this experiment was to investigate whether systemic administration of Ab728, a surrogate for Ab327, was able to prevent or attenuate Sjögren's Syndrome development in NOD mice.

Female NOD mice were treated with Ab728 or isotype control mIgG1 (20 mg/kg/week) starting at 7 weeks of age. Mice were sacrificed at 18 weeks of age and salivary glands were harvested. A piece of salivary gland was fixed with 1.6% PFA 20% sucrose at 4° C. overnight, embedded in OCT and stored at −80° C. until analysis by immunofluorescence. Another piece was frozen in liquid nitrogen for mRNA studies.

In NOD mice, focal inflammation in the submandibular salivary glands and the lacrimal glands develops from approximately 8 weeks of age onwards. The foci appear comparable in structure and cellular composition with infiltrates found in some human salivary glands, with presence of T and B cells. To investigate if anti-IL-21 treatment alleviated lymphocytic infiltration in the NOD salivary gland, immunofluorescence staining was performed. Briefly, 8 μm frozen sections of salivary glands were washed with PBS and then incubated for 1 h at room temperature with purified primary antibodies, followed by incubation with the appropriate labeled secondary antibodies for 30 min. Primary antibodies were anti-CD3 (T cells) and anti-B220 (B cells) from BD Biosciences. Secondary antibodies were Alexa Fluor 488 goat anti-rat IgG and DyLight 594 goat anti-Armenian hamster from Jackson ImmunoResearch Laboratories. DAPI was used to identify the nucleus of cells.

Figure 6:
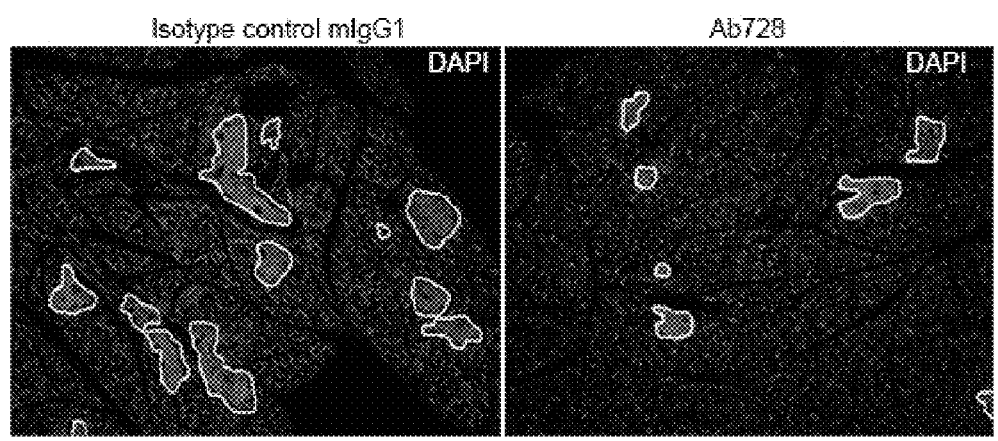

NOD mice treated with mIgG1 control antibody showed the presence of typical lymphomonocytic infiltrates arranged as periductal aggregates with T and B lymphocytes (FIG. 6) highly organized resembling lymphocytic foci found in Sjögren's Syndrome patients. Ab728 treatment efficiently decreased not only the number but also the size of foci observed.

The development of lymphoid aggregates in Sjögren's Syndrome is thought to be regulated by the ectopic production of the lymphoid chemokine CXCL13 and its cognate receptor CXCR5, which regulate the recirculation and positioning of B cells and CD4+ T follicular helper (TFH) cells into the germinal center structures. It has been shown that IL-21 is involved in the maintenance of TFH and germinal center structures. IL-21 also controls the activation of CD8+ T lymphocytes, which are thought to destroy target cells via perforin and granzymes. To investigate if anti-IL-21 treatment would decrease the expression of those markers, total RNA was isolated from frozen salivary glands by homogenization in Trizol followed by RNeasy Mini kit (Qiagen, Inc.). RNA concentrations were determined from spectrophotometric absorption at 260 nm. RNA was reverse-transcribed into cDNA using High-Capacity cDNA Reverse Transcription Kit (PE Applied Biosystems). All reactions were performed in triplicate to determine the relative abundance of assayed mRNAs. Primer probe sets for IL-21 (Mm00517640_m1), CXCR5 (Mm00432086_m1), CXCL13 (Mm04214185_s1), CCR9 (Mm02620030_s1), Granzyme B (Mm00442834_m1) and CD8 (Mm01182107_g1) were obtained from PE Applied Biosystems. GusB (Mm00446956_m1) was measured as endogenous controls to normalize variability in gene expression levels. Expression data were analyzed using Delta Ct method. Individual Ct values were calculated as means of triplicate measurements.

Figure 5:
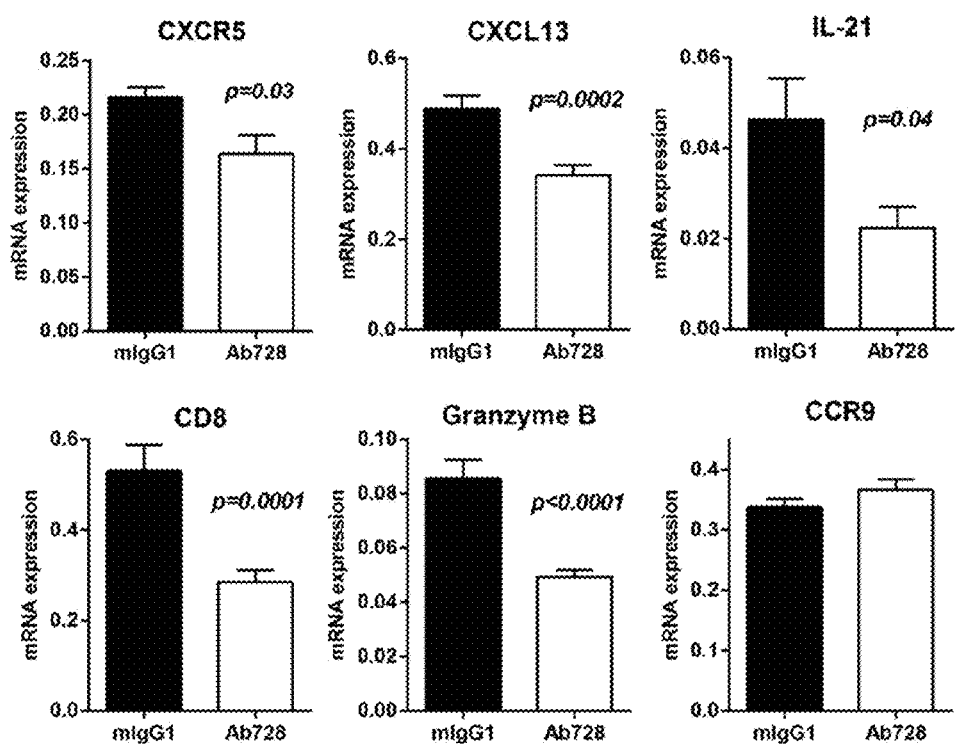
FIGS. 5 and 6. Treatment with anti-mouse IL-21 antibody is shown to alleviate lymphocytic infiltration in salivary glands of NOD mice by mRNA analysis (FIG. 5) and histological analysis (FIG. 6, lymphocytes are outlined).

CXCL13, CXCR5, IL-21, CD8 and Granzyme B mRNA transcripts were statistically significantly down-regulated in Ab728 treated mice, as compared with mIgG1 control antibody treated mice. FIG. 5 shows the mRNA analysis in salivary glands of mice. It can be seen that treatment modulates the expression of proteins involved in the disease. In summary, administration of an anti-mouse IL-21 antibody (Ab728) decreased lymphocytic infiltration into salivary glands and delayed the development of SS-like symptoms of NOD mice.

Anti-mIL-21 (Ab728) Treatment Prevents Diabetes in NOD Mice.

Ab728 is a murine IgG1 monoclonal antibody that binds specifically to mouse IL-21. The binding affinity of murine IL-21 to surrogate Ab728 is 1 pM. Ab728 was able to completely neutralize murine IL-21 in in vivo and in vitro assays.

Human type I diabetes is an autoimmune disease that results from the autoreactive destruction of the insulin-producing-beta cells in the islets of Langerhans of the pancreas, which leads to the subsequent loss of insulin production. The non-obese diabetic (NOD) strain of mice develops a similar disease and also serves as a model system for studying the mechanisms involved in the initiation and propagation of the autoimmune response. Histological studies have shown that few immune cell infiltrates are noted in islets until approximately 3 to 4 weeks of age, when both male and female mice begin to demonstrate mononuclear infiltrates that surround the islet (peri-insulitis). These infiltrate progress and invade the islets (insulitis) followed by hyperglycemia and full-blown diabetes beginning approximate at 12 weeks of age.

Previous work showed that deletion of IL-21 signaling in NOD mice leads to almost complete abrogation of disease development (Spolski R, et al. IL-21 signaling is critical for the development of type I diabetes in the NOD mouse. Proc Natl Acad Sci USA 2008; 105:14028, 2008). The aim of the experiment was to investigate whether systemic administration of Ab728 was able to prevent or attenuate diabetes development in NOD mice.

Female NOD mice were treated with Ab728 or isotype control mIgG1 (20 mg/kg/week) at different periods of time in the disease process. A group of mice started treatment at 7 weeks of age (prevention study, FIG. 7A) and another group of animals started treatment at 13 weeks of age (late preclinical stage, FIG. 7B). In both situations, mice were followed for diabetes development until mice were 37 weeks of age. To track the development of diabetes, blood glucose levels were monitored weekly and animals were considered diabetic if blood glucose was above 250 mg/dl in two consecutive measurements. Exposure to Ab728 was confirmed by quantitative ELISA.

NOD mice treated with mIgG1 control antibody started to develop diabetes when they were between 13-15 weeks of age and 75% of mice progressed to overt diabetes by 37 weeks of age (9 of 12 mice for prevention and 6 of 8 mice for late preclinical stage—see FIG. 7A and FIG. 7B). In contrast, anti-IL-21 treatment significantly delayed diabetes progression. Only one out of 12 mice (8%, FIG. 7A, p=0.0007) developed diabetes when treatment began at 7 weeks of age and only one out of eleven mice (9%, FIG. 7B, p=0.002) progressed to overt diabetes when treatment began during the late preclinical stage.

In summary, administration of an anti-mouse IL-21 antibody (Ab728) efficiently prevented diabetes development in NOD mice.

Sequences
Ab327 Amino Acid Sequences

| SEQ ID NO: | Identity | Length | Sequence |
|---|---|---|---|
| 1 | Heavy Chain Variable Domain | 117 | QVQLVQSGAEVKKPGASVKVSCKASGY TFTDYWMHWVRQAPGQGLEWMGLIDTS DVYTIYNQKFKGRVTMTRDTSTSTVYM ELSSLRSEDTAVYYCARYGPLAMDYWG QGTLVTVSS |
| 2 | Light Chain Variable Domain | 106 | DIQMTQSPSSLSASVGDRVTITCRASQ DISNYLNWYQQKPGKAPKLLIYYTSRL HSGVPSRFSGSGSGTDFTLTISSLQPE DFATYYCQQFHTLRTFGGGTKVEIK |
| 3 | Heavy Chain | 443 | QVQLVQSGAEVKKPGASVKVSCKASGY TFTDYWMHWVRQAPGQGLEWMGLIDTS DVYTIYNQKFKGRVTMTRDTSTSTVYM ELSSLRSEDTAVYYCARYGPLAMDYWG QGTLVTVSSASTKGPSVFPLAPCSRST SESTAALGCLVKDYFPEPVTVSWNSGA LTSGVHTFPAVLQSSGLYSLSSVVTVP SSSLGTKTYTCNVDHKPSNTKVDKRVE SKYGPPCPPCPAPEAAGGPSVFLFPPK PKDTLMISRTPEVTCVVVDVSQEDPEV QFNWYVDGVEVHNAKTKPREEQFNSTY RVVSVLTVLHQDWLNGKEYKCKVSNKG LPSSIEKTISKAKGQPREPQVYTLPPS QEEMTKNQVSLTCLVKGFYPSDIAVEW ESNGQPENNYKTTPPVLDSDGSFFLYS RLTVDKSRWQEGNVFSCSVMHEALHNH YTQKSLSLSLG |
| 4 | Light Chain | 213 | DIQMTQSPSSLSASVGDRVTITCRASQ DISNYLNWYQQKPGKAPKLLIYYTSRL HSGVPSRFSGSGSGTDFTLTISSLQPE DFATYYCQQFHTLRTFGGGTKVEIKRT VAAPSVFIFPPSDEQLKSGTASVVCLL NNFYPREAKVQWKVDNALQSGNSQESV TEQDSKDSTYSLSSTLTLSKADYEKHK VYACEVTHQGLSSPVTKSFNRGEC |
| 7 | LC-CDR1 | 11 | RASQDISNYLN |
| 8 | LC-CDR2 | 8 | YYTSRLHS |
| 9 | LC-CDR3 | 8 | QQFHTLRT |
| 10 | HC-CDR1 | 13 | KASGYTFTDYWMH |
| 11 | HC-CDR2 | 17 | LIDTSDVYTIYNQKFKG |
| 12 | HC-CDR3 | 10 | ARYGPLAMDY |

The following sequences were used in the Example and Assays.

HUMAN IL-21- UniprotKB/Swiss-Prot database entry#Q9HBE4
(SEQ ID NO: 13)
QDRHMIRMRQLIDIVDQLKNYVNDLVPEFLPAPEDVETNCEW

SAFSCFQKAQLKSANTGNNERIINVSIKKLKRKPPSTNAGRR

QKHRLTCPSCDSYEKKPPKEFLERFKSLLQKMIHQHLSSRTH

GSEDS

CYNO IL-21-- Sequence was cloned in-house; not available in public database
(SEQ ID NO: 14)
QDRHMIRMRQLIDIVDQLKNYVNDLDPEFLPAPEDVETNCEW

SAISCFQKAQLKSANTGNNERIINLSIKKLKRKSPSTGAERR

-continued

QKHRLTCPSCDSYEKKPPKEFLERFKSLLQKMIHQHLSSRTH

GSEDS

MOUSE IL-21- UniprotKB/Swiss-Prot database
entry#Q9ES17
(SEQ ID NO: 15)
HKSSPQGPDRLLIRLRHLIDIVEQLKIYENDLDPELLSAPQD

VKGHCEHAAFACFQKAKLKPSNPGNNKTFIIDLVAQLRRRLP

ARRGGKKQKHIAKCPSCDSYEKRTPKEFLERLKWLLQKMIHQ

HLS

RAT IL-21- UniprotKB/Swiss-Prot database
entry#A3QPB9
(SEQ ID NO: 16)
HKSSPQRPDHLLIRLRHLMDIVEQLKIYENDLDPELLTAPQD

VKGQCEHEAFACFQKAKLKPSNTGNNKTFINDLLAQLRRRLP

AKRTGNKQRHMAKCPSCDLYEKKTPKEFLERLKWLLQKMIHQ

HLS

RABBIT IL-21- (COMMERCIAL REAGENT- R&D
Systems, cat#7274-RB/CF)
(SEQ ID NO: 17)
HKSSSKGQDRYMIRMHQLLDIVDQLQSDVNDLDPDFLPAPQD

VQKGCEQSAFSCFQKAQLKPANAGDNGKRISSLIKQLKRKLP

STKSKKTQKHRPTCPSCYSYEKKNLKEFLERLKSLIQKMIHQ

HLLEHLR

DNA for expressing Ab327

| SEQ ID NO: | Identity | Length | Sequence |
|---|---|---|---|
| 5 | Heavy Chain | | caggtgcagctggtgcagtctgggg
ctgaggtgaagaagcctggggcctc
agtgaaggtttcctgcaaggcatct
ggctacacattcactgactactgga
tgcactgggtgcgacaggcccctgg
acaagggcttgagtggatgggactg
attgatacttctgatgtttatacta
tctacaatcaaaagttcaagggcag
agtcaccatgaccagggacacgtcc
acgagcacagtctacatggagctga
gcagcctgagatctgaggacacggc
cgtgtattactgtgcaagatatggg
cccctggctatggactactggggcc
agggcacccctggtcaccgtctcctc
agcctccaccaaggggcccatcggtc
ttcccgctagcgccctgctccagga
gcacctccgagagcacagccgccct
gggctgcctggtcaaggactacttc
cccgaaccggtgacggtgtcgtgga
actcaggcgccctgaccagcggcgt
gcacaccttcccggctgtcctacag
tcctcaggactctactccctcagca |

DNA for expressing Ab327

| SEQ ID NO: | Identity | Length | Sequence |
|---|---|---|---|
| | | | gcgtggtgaccgtgccctccagcag
cttgggcacgaagacctacacctgc
aacgtagatcacaagcccagcaaca
ccaaggtggacaagagagttgagtc
caaatatggtccccatgcccaccc
tgcccagcacctgaggccgccgggg
gaccatcagtcttcctgttcccccc
aaaaccaaggacactctcatgatc
tcccggacccctgaggtcacgtgcg
tggtggtggacgtgagccaggaaga
ccccgaggtccagttcaactggtac
gtggatggcgtggaggtgcataatg
ccaagacaaagccgcgggaggagca
gttcaacagcacgtaccgtgtggtc
agcgtcctcaccgtcctgcaccagg
actggctgaacggcaaggagtacaa
gtgcaaggtctccaacaaaggcctc
ccgtcctccatcgagaaaaccatct
ccaaagccaaagggcagccccgaga
gccacaggtgtacaccctgcccccca
tcccaggaggagatgaccaagaacc
aggtcagcctgacctgcctggtcaa
aggcttctaccccagcgacatcgcc
gtggagtgggaaagcaatgggcagc
cggagaacaactacaagaccacgcc
tcccgtgctggactccgacggctcc
ttcttcctctacagcaggctaaccg
tggacaagagcaggtggcaggaggg
gaatgtcttctcatgctccgtgatg
catgaggctctgcacaaccactaca
cacagaagagcctctccctgtctct
gggt |
| 6 | Light Chain | | gacatccagatgacccagtctccat
cctccctgtctgcatctgtaggaga
cagagtcaccatcacttgcagggca
agtcaggacattagcaattattaa
actggtatcagcagaaaccagggaa
agcccctaagctcctgatctattac
acatcaagattacactcaggggtcc
catcaaggttcagtggcagtggatc
tgggacagatttcactctcaccatc
agcagtctgcaacctgaagattttg
caacttactactgtcaacagtttca
cacgcttcggcgcttcggcggaggg
accaaggtggagatcaaaagaactg
tggcggcgccatctgtcttcatctt
cccgccatctgatgagcagttgaaa
tccggaactgcctctgttgtgtgcc
tgctgaataacttctatcccagaga
ggccaaagtacagtggaaggtggat
aacgccctccaatcgggtaactccc
aggagagtgtcacagagcaggacag
caaggacagcacctacagcctcagc
agcaccctgacgctgagcaaagcag
actacgagaaacacaaagtctacgc
ctgcgaagtcacccatcagggcctg
agctcgcccgtcacaaagagcttca
acaggggagagtgc |

We claim:

1. An antibody that binds to human IL-21, comprising a heavy chain variable region (HCVR) and a light chain variable region (LCVR), wherein the LCVR comprises SEQ ID NO:7 at CDRL1, SEQ ID NO:8 at CDRL2 and SEQ ID NO:9 at CDRL3 and wherein the HCVR comprises SEQ ID NO:10 at CDRH1, SEQ ID NO:11 at CDRH2 and SEQ ID NO:12 at CDRH3.

2. The antibody of claim 1, comprising two heavy chain variable regions (HCVRs) and two light chain variable regions (LCVRs), wherein each LCVR comprises SEQ ID NO:7 at CDRL1, SEQ ID NO:8 at CDRL2 and SEQ ID NO:9 at CDRL3 and wherein each HCVR comprises SEQ ID NO:10 at CDRH1, SEQ ID. NO:11 at CDRH2 and SEQ ID NO:12 at CDRH3.

3. A pharmaceutical composition comprising the antibody of claim 2 and a pharmaceutically-acceptable excipient.

4. The antibody of claim 1, comprising an antibody heavy chain and an antibody light chain, wherein the heavy chain comprises a heavy chain variable region, the amino acid sequence of which is SEQ ID NO:1, and wherein the light chain comprises a light chain variable region, the amino acid sequence of which is SEQ ID NO:2.

5. The antibody of claim 4, comprising two antibody heavy chains and two antibody light chains, in which each heavy chain comprises a heavy chain variable region, the amino acid sequence of which is SEQ ID NO:1, and in which each light chain comprises a light chain variable region, the amino acid sequence of which is SEQ ID NO:2.

6. A pharmaceutical composition comprising the antibody of claim 5 and a pharmaceutically-acceptable excipient.

7. The antibody of claim 5, comprising two antibody heavy chains and two antibody light chains, in which the amino acid sequence of each heavy chain is t SEQ ID NO:3 and the amino acid sequence of each light chain is SEQ ID NO:4.

8. A pharmaceutical composition comprising the antibody of claim 7 and a pharmaceutically-acceptable excipient.

9. A method of treating an autoimmune condition in a patient comprising administering an effective dose of the antibody of claim 2 to the patient, wherein the autoimmune condition is primary Sjögren's Syndrome, Sjögren's Syndrome, Systemic Lupus Erythematosus, Grave's disease, or type 1 diabetes.

10. The method of claim 9 in which the autoimmune condition is primary Sjögren's Syndrome or Sjögren's Syndrome.

11. The method of claim 9 in which the autoimmune condition is Systemic Lupus Erythematosus.

12. A method of treating an autoimmune condition in a patient comprising administering an effective dose of the antibody of claim 5 to the patient, wherein the autoimmune condition is primary Sjögren's Syndrome, Sjögren's Syndrome, Systemic Lupus Erythematosus, Grave's disease, or type 1 diabetes.

13. A method of treating an autoimmune condition in a patient comprising administering an effective dose of the antibody of claim 7 to the patient, wherein the autoimmune condition is primary Sjögren's Syndrome, Sjögren's Syndrome, Systemic Lupus Erythematosus, Grave's disease, or type 1 diabetes.

14. A DNA molecule comprising a polynucleotide that encodes an antibody heavy chain whose amino acid sequence is SEQ ID NO:3.

15. The DNA molecule of claim 14 in which the sequence of the polynucleotide that encodes the antibody heavy chain is SEQ ID NO:5.

16. A DNA molecule comprising a polynucleotide that encodes an antibody light chain whose amino acid sequence is SEQ ID NO:4.

17. The DNA molecule of claim 16 in which the sequence of the polynucleotide that encodes the antibody light chain is SEQ ID NO:6.

18. A DNA molecule comprising a polynucleotide that encodes an antibody heavy chain whose amino acid sequence is SEQ ID NO:3 and comprising a polynucleotide that encodes an antibody light chain whose amino acid sequence is SEQ ID NO:4.

19. An isolated mammalian cell transformed with the DNA molecule of claim 18, which transformed mammalian cell is capable of expressing an antibody comprising two antibody heavy chains and two antibody light chains, in which the amino sequence of each of the two heavy chains is SEQ ID NO:3 and the amino acid sequence of each of the two light chains is SEQ ID NO:4.

20. A process for producing an antibody, which antibody comprises two antibody heavy chains and two antibody light chains, in which the amino sequence of each of the two heavy chains is SEQ ID NO:3 and the amino acid sequence of each of the two light chains is SEQ ID NO:4, and which process comprises:
   a. cultivating the mammalian cell of claim 19 under conditions such that the antibody is expressed, and
   b. recovering the expressed antibody.

21. An antibody produced by the process of claim 20.

22. A pharmaceutical composition comprising the antibody of claim 21 and a pharmaceutically-acceptable excipient.

23. A method of treating an autoimmune condition in a patient comprising administering an effective dose of the antibody of claim 21 to the patient, wherein the autoimmune condition is primary Sjögren's Syndrome, Sjögren's Syndrome, Systemic Lupus Erythematosus, Grave's disease, or type 1 diabetes.

24. An antibody produced by
   a. cultivating a mammalian cell that comprises a polynucleotide s encoding the antibody heavy chain having the amino acid of SEQ ID NO:3 and a polynucleotide sequence encoding the antibody light chain having the amino acid sequence of SEQ ID NO:4 under conditions such that the antibody heavy and light chains are expressed, and
   b. recovering the expressed antibody.

25. A pharmaceutical composition comprising the antibody of claim 24 and one or more pharmaceutically acceptable carriers, diluents or excipients.

26. An antibody produced by
   a. cultivating a mammalian cell that is transformed with a DNA molecule comprising a polynucleotide sequence that encodes the antibody heavy chain having the amino acid sequence of SEQ ID NO:3 and a polynucleotide sequence that encodes the antibody light chain having the amino acid sequence of SEQ ID NO:4 under conditions such that the antibody heavy and light chains are expressed, and
   b. recovering the expressed antibody.

27. A pharmaceutical composition comprising the antibody of claim 26 and one or more pharmaceutically acceptable carriers, diluents or excipients.

* * * * *

SEQUENCE LISTING

<160> NUMBER OF SEQ ID NOS: 17

<210> SEQ ID NO 1
<211> LENGTH: 117
<212> TYPE: PRT
<213> ORGANISM: Artificial Sequence
<220> FEATURE:

<223> OTHER INFORMATION: synthetic construct

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Leu Ile Asp Thr Ser Asp Val Tyr Thr Ile Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Pro Leu Ala Met Asp Tyr Trp Gly Gln Gly Thr Leu
            100                 105                 110

Val Thr Val Ser Ser
            115

<210> SEQ ID NO 2
<211> LENGTH: 106
<212> TYPE: PRT
<213> ORGANISM: Artificial Sequence
<220> FEATURE:
<223> OTHER INFORMATION: synthetic construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Tyr Thr
                85                  90                  95

Phe Gly Gly Gly Thr Lys Val Glu Ile Lys
            100                 105

<210> SEQ ID NO 3
<211> LENGTH: 443
<212> TYPE: PRT
<213> ORGANISM: Artificial Sequence
<220> FEATURE:
<223> OTHER INFORMATION: synthetic construct

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Leu Ile Asp Thr Ser Asp Val Tyr Thr Ile Tyr Asn Gln Lys Phe

```
            50                  55                  60
Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Tyr Gly Pro Leu Ala Met Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
                290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly
                435                 440

<210> SEQ ID NO 4
<211> LENGTH: 213
<212> TYPE: PRT
<213> ORGANISM: Artificial Sequence
```

<220> FEATURE:
<223> OTHER INFORMATION: synthetic construct

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Thr Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 5
<211> LENGTH: 1329
<212> TYPE: DNA
<213> ORGANISM: Artificial Sequence
<220> FEATURE:
<223> OTHER INFORMATION: synthetic construct

<400> SEQUENCE: 5

```
caggtgcagc tggtgcagtc tggggctgag gtgaagaagc ctggggcctc agtgaaggtt      60
tcctgcaagg catctggcta cacattcact gactactgga tgcactgggt gcgacaggcc     120
cctggacaag gcttgagtg gatgggactg attgatactt ctgatgttta tactatctac      180
aatcaaaagt tcaagggcag agtcaccatg accagggaca cgtccacgag cacagtctac     240
atggagctga gcagcctgag atctgaggac acggccgtgt attactgtgc aagatatggg     300
cccctggcta tggactactg gggccagggc accctggtca ccgtctcctc agcctccacc     360
aagggcccat cggtcttccc gctagcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
```

```
cccccatgcc cacctgccc agcacctgag gccgccgggg gaccatcagt cttcctgttc    720 ccccaaaac ccaaggacac tctcatgatc tcccggaccc ctgaggtcac gtgcgtggtg    780
gtggacgtga gccaggaaga ccccgaggtc cagttcaact ggtacgtgga tggcgtggag    840
gtgcataatg ccaagacaaa gccgcgggag gagcagttca acagcacgta ccgtgtggtc    900
agcgtcctca ccgtcctgca ccaggactgg ctgaacggca aggagtacaa gtgcaaggtc    960
tccaacaaag gcctcccgtc ctccatcgag aaaaccatct ccaaagccaa agggcagccc   1020
cgagagccac aggtgtacac cctgccccca tcccaggagg agatgaccaa gaaccaggtc   1080
agcctgacct gcctggtcaa aggcttctac cccagcgaca tcgccgtgga gtgggaaagc   1140
aatgggcagc cggagaacaa ctacaagacc acgcctcccg tgctggactc cgacggctcc   1200
ttcttcctct acagcaggct aaccgtggac aagagcaggt ggcaggaggg gaatgtcttc   1260
tcatgctccg tgatgcatga ggctctgcac aaccactaca cacagaagag cctctcctg    1320 tctctgggt                                                           1329
```

<210> SEQ ID NO 6
<211> LENGTH: 639
<212> TYPE: DNA
<213> ORGANISM: Artificial Sequence
<220> FEATURE:
<223> OTHER INFORMATION: synthetic construct

<400> SEQUENCE: 6

```
gacatccaga tgacccagtc tccatcctcc ctgtctgcat ctgtaggaga cagagtcacc     60
atcacttgca gggcaagtca ggacattagc aattatttaa actggtatca gcagaaacca    120
gggaaagccc ctaagctcct gatctattac acatcaagat tacactcagg ggtcccatca    180
aggttcagtg gcagtggatc tgggacagat ttcactctca ccatcagcag tctgcaacct    240
gaagattttg caacttacta ctgtcaacag tttcacacgc ttcggacgtt cggcggaggg    300
accaaggtgg agatcaaaag aactgtggcg gcgccatctg tcttcatctt cccgccatct    360
gatgagcagt tgaaatccgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgc                           639
```

<210> SEQ ID NO 7
<211> LENGTH: 11
<212> TYPE: PRT
<213> ORGANISM: Artificial Sequence
<220> FEATURE:
<223> OTHER INFORMATION: synthetic construct

<400> SEQUENCE: 7

Arg Ala Ser Gln Asp Ile Ser Asn Tyr Leu Asn
1               5                   10

<210> SEQ ID NO 8
<211> LENGTH: 8
<212> TYPE: PRT
<213> ORGANISM: Artificial Sequence
<220> FEATURE:
<223> OTHER INFORMATION: synthetic construct

<400> SEQUENCE: 8

Tyr Tyr Thr Ser Arg Leu His Ser
1               5

<210> SEQ ID NO 9
<211> LENGTH: 8
<212> TYPE: PRT
<213> ORGANISM: Artificial Sequence
<220> FEATURE:
<223> OTHER INFORMATION: synthetic construct

<400> SEQUENCE: 9

Gln Gln Phe His Thr Leu Arg Thr
1               5

<210> SEQ ID NO 10
<211> LENGTH: 13
<212> TYPE: PRT
<213> ORGANISM: Artificial Sequence
<220> FEATURE:
<223> OTHER INFORMATION: synthetic construct

<400> SEQUENCE: 10

Lys Ala Ser Gly Tyr Thr Phe Thr Asp Tyr Trp Met His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: synthetic construct

<400> SEQUENCE: 11

Leu Ile Asp Thr Ser Asp Val Tyr Thr Ile Tyr Asn Gln Lys Phe Lys
1               5                   10                  15

Gly

<210> SEQ ID NO 12
<211> LENGTH: 10
<212> TYPE: PRT
<213> ORGANISM: Artificial Sequence
<220> FEATURE:
<223> OTHER INFORMATION: synthetic construct

<400> SEQUENCE: 12

Ala Arg Tyr Gly Pro Leu Ala Met Asp Tyr
1               5                   10

<210> SEQ ID NO 13
<211> LENGTH: 131
<212> TYPE: PRT
<213> ORGANISM: Artificial Sequence
<220> FEATURE:
<223> OTHER INFORMATION: This protein was recombinantly produced and is
      identical to the homo sapien sequence.

<400> SEQUENCE: 13

Gln Asp Arg His Met Ile Arg Met Arg Gln Leu Ile Asp Ile Val Asp
1               5                   10                  15

Gln Leu Lys Asn Tyr Val Asn Asp Leu Val Pro Glu Phe Leu Pro Ala
                20                  25                  30

Pro Glu Asp Val Glu Thr Asn Cys Glu Trp Ser Ala Phe Ser Cys Phe
            35                  40                  45

Gln Lys Ala Gln Leu Lys Ser Ala Asn Thr Gly Asn Asn Glu Arg Ile
        50                  55                  60

```
Ile Asn Val Ser Ile Lys Lys Leu Lys Arg Lys Pro Pro Ser Thr Asn
 65                  70                  75                  80

Ala Gly Arg Arg Gln Lys His Arg Leu Thr Cys Pro Ser Cys Asp Ser
                 85                  90                  95

Tyr Glu Lys Lys Pro Pro Lys Glu Phe Leu Glu Arg Phe Lys Ser Leu
                100                 105                 110

Leu Gln Lys Met Ile His Gln His Leu Ser Ser Arg Thr His Gly Ser
            115                 120                 125

Glu Asp Ser
    130

<210> SEQ ID NO 14
<211> LENGTH: 131
<212> TYPE: PRT
<213> ORGANISM: Artificial Sequence
<220> FEATURE:
<223> OTHER INFORMATION: This protein was recombinantly produced and is
      identical to the Cynomolgus monkey sequence.

<400> SEQUENCE: 14

Gln Asp Arg His Met Ile Arg Met Arg Gln Leu Ile Asp Ile Val Asp
  1               5                  10                  15

Gln Leu Lys Asn Tyr Val Asn Asp Leu Asp Pro Glu Phe Leu Pro Ala
                 20                  25                  30

Pro Glu Asp Val Glu Thr Asn Cys Glu Trp Ser Ala Ile Ser Cys Phe
             35                  40                  45

Gln Lys Ala Gln Leu Lys Ser Ala Asn Thr Gly Asn Asn Glu Arg Ile
 50                  55                  60

Ile Asn Leu Ser Ile Lys Lys Leu Lys Arg Lys Ser Pro Ser Thr Gly
 65                  70                  75                  80

Ala Glu Arg Arg Gln Lys His Arg Leu Thr Cys Pro Ser Cys Asp Ser
                 85                  90                  95

Tyr Glu Lys Lys Pro Pro Lys Glu Phe Leu Glu Arg Phe Lys Ser Leu
                100                 105                 110

Leu Gln Lys Met Ile His Gln His Leu Ser Ser Arg Thr His Gly Ser
            115                 120                 125

Glu Asp Ser
    130

<210> SEQ ID NO 15
<211> LENGTH: 129
<212> TYPE: PRT
<213> ORGANISM: Artificial Sequence
<220> FEATURE:
<223> OTHER INFORMATION: This protein was recombinantly produced and is
      identical to the mus musculus sequence.

<400> SEQUENCE: 15

His Lys Ser Ser Pro Gln Gly Pro Asp Arg Leu Leu Ile Arg Leu Arg
  1               5                  10                  15

His Leu Ile Asp Ile Val Glu Gln Leu Lys Ile Tyr Glu Asn Asp Leu
                 20                  25                  30

Asp Pro Glu Leu Leu Ser Ala Pro Gln Asp Val Lys Gly His Cys Glu
             35                  40                  45

His Ala Ala Phe Ala Cys Phe Gln Lys Ala Lys Leu Lys Pro Ser Asn
 50                  55                  60

Pro Gly Asn Asn Lys Thr Phe Ile Ile Asp Leu Val Ala Gln Leu Arg
 65                  70                  75                  80
```

```
Arg Arg Leu Pro Ala Arg Gly Gly Lys Lys Gln Lys His Ile Ala
                85                  90                  95

Lys Cys Pro Ser Cys Asp Ser Tyr Glu Lys Arg Thr Pro Lys Glu Phe
            100                 105                 110

Leu Glu Arg Leu Lys Trp Leu Leu Gln Lys Met Ile His Gln His Leu
        115                 120                 125

Ser

<210> SEQ ID NO 16
<211> LENGTH: 129
<212> TYPE: PRT
<213> ORGANISM: Artificial Sequence
<220> FEATURE:
<223> OTHER INFORMATION: This protein was recombinantly produced and is
      identical to the rattus norvegicus sequence.

<400> SEQUENCE: 16

His Lys Ser Ser Pro Gln Arg Pro Asp His Leu Leu Ile Arg Leu Arg
1               5                   10                  15

His Leu Met Asp Ile Val Glu Gln Leu Lys Ile Tyr Glu Asn Asp Leu
            20                  25                  30

Asp Pro Glu Leu Leu Thr Ala Pro Gln Asp Val Lys Gly Gln Cys Glu
        35                  40                  45

His Glu Ala Phe Ala Cys Phe Gln Lys Ala Lys Leu Lys Pro Ser Asn
    50                  55                  60

Thr Gly Asn Asn Lys Thr Phe Ile Asn Asp Leu Leu Ala Gln Leu Arg
65                  70                  75                  80

Arg Arg Leu Pro Ala Lys Arg Thr Gly Asn Lys Gln Arg His Met Ala
                85                  90                  95

Lys Cys Pro Ser Cys Asp Leu Tyr Glu Lys Lys Thr Pro Lys Glu Phe
            100                 105                 110

Leu Glu Arg Leu Lys Trp Leu Leu Gln Lys Met Ile His Gln His Leu
        115                 120                 125

Ser

<210> SEQ ID NO 17
<211> LENGTH: 133
<212> TYPE: PRT
<213> ORGANISM: Artificial Sequence
<220> FEATURE:
<223> OTHER INFORMATION: This protein was recombinantly produced and is
      identical to the oryctolagus cuniculus sequence.

<400> SEQUENCE: 17

His Lys Ser Ser Lys Gly Gln Asp Arg Tyr Met Ile Arg Met His
1               5                   10                  15

Gln Leu Leu Asp Ile Val Asp Gln Leu Gln Ser Asp Val Asn Asp Leu
            20                  25                  30

Asp Pro Asp Phe Leu Pro Ala Pro Gln Asp Val Gln Lys Gly Cys Glu
        35                  40                  45

Gln Ser Ala Phe Ser Cys Phe Gln Lys Ala Gln Leu Lys Pro Ala Asn
    50                  55                  60

Ala Gly Asp Asn Gly Lys Arg Ile Ser Ser Leu Ile Lys Gln Leu Lys
65                  70                  75                  80

Arg Lys Leu Pro Ser Thr Lys Ser Lys Lys Thr Gln Lys His Arg Pro
                85                  90                  95

Thr Cys Pro Ser Cys Tyr Ser Tyr Glu Lys Lys Asn Leu Lys Glu Phe
```

-continued

```
            100                 105                 110
Leu Glu Arg Leu Lys Ser Leu Ile Gln Lys Met Ile His Gln His Leu
            115                 120                 125

Leu Glu His Leu Arg
    130
```